(12) United States Patent
Staats

(10) Patent No.: US 6,800,849 B2
(45) Date of Patent: Oct. 5, 2004

(54) MICROFLUIDIC ARRAY DEVICES AND METHODS OF MANUFACTURE AND USES THEREOF

(76) Inventor: Sau Lan Tang Staats, 609 Ramsey Rd., Hockessin, DE (US) 19707

( * ) Notice: Subject to any disclaimer, the term of this patent is extended or adjusted under 35 U.S.C. 154(b) by 61 days.

(21) Appl. No.: 10/174,343

(22) Filed: Jun. 17, 2002

(65) Prior Publication Data

US 2003/0111599 A1 Jun. 19, 2003

Related U.S. Application Data

(60) Provisional application No. 60/341,069, filed on Dec. 19, 2001.

(51) Int. Cl.[7] .......................... B01D 59/44; H01J 49/00
(52) U.S. Cl. ................................ 250/288; 250/423 R
(58) Field of Search .................... 250/423 R, 424, 250/428, 432 R, 435, 288; 239/424.5

(56) References Cited

U.S. PATENT DOCUMENTS

| | | | |
|---|---|---|---|
| 4,756,884 A | | 7/1988 | Hillman et al. |
| 5,306,412 A | * | 4/1994 | Whitehouse et al. ....... 204/452 |
| 5,486,335 A | | 1/1996 | Wilding et al. |
| 5,900,130 A | | 5/1999 | Benvegnu et al. |
| 5,992,820 A | | 11/1999 | Fare et al. |
| 6,042,709 A | | 3/2000 | Parce et al. |
| 6,068,751 A | | 5/2000 | Neukermans |
| 6,136,212 A | | 10/2000 | Mastrangelo et al. |
| 6,137,501 A | | 10/2000 | Wen et al. |
| 6,627,882 B2 | * | 9/2003 | Schultz et al. .............. 250/288 |
| 2002/0113144 A1 | * | 8/2002 | Huang et al. ............. 239/424.5 |

OTHER PUBLICATIONS

International Search Report.

* cited by examiner

Primary Examiner—John R. Lee
Assistant Examiner—Erin-Michael Gill
(74) Attorney, Agent, or Firm—Darby & Darby

(57) ABSTRACT

Microfluidic nozzle array devices are provided with the body of each device having at least one nozzle extending outwardly from one surface of the body. Each nozzle includes a tip opening having a diameter of equal to or less than about 100 μm, preferably 50 μm, and more preferably 20 μm and an outer diameter of nozzle is equal to or less than about 150 μm, preferably 100 μm, and more preferably 50 μm. The microfluidic nozzle array devices are fabricated using an injection molding process and find particular utility in a wide range of applications, including but not limited to nanospray/electrospray applications, mass spectrometer applications, optical spectrometry applications, spotting applications (i.e., DNA or protein array), etc.

56 Claims, 15 Drawing Sheets

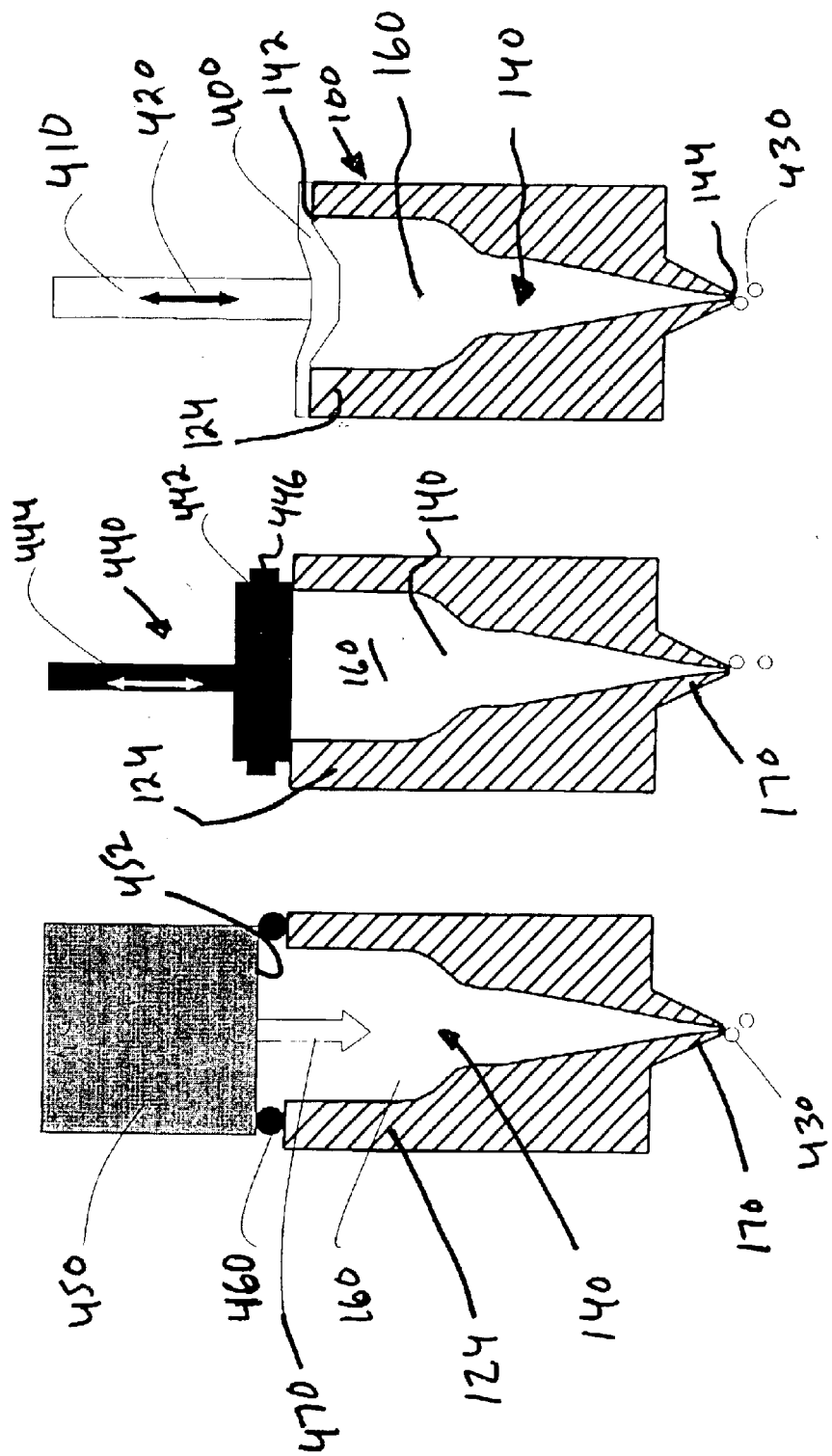

Front view

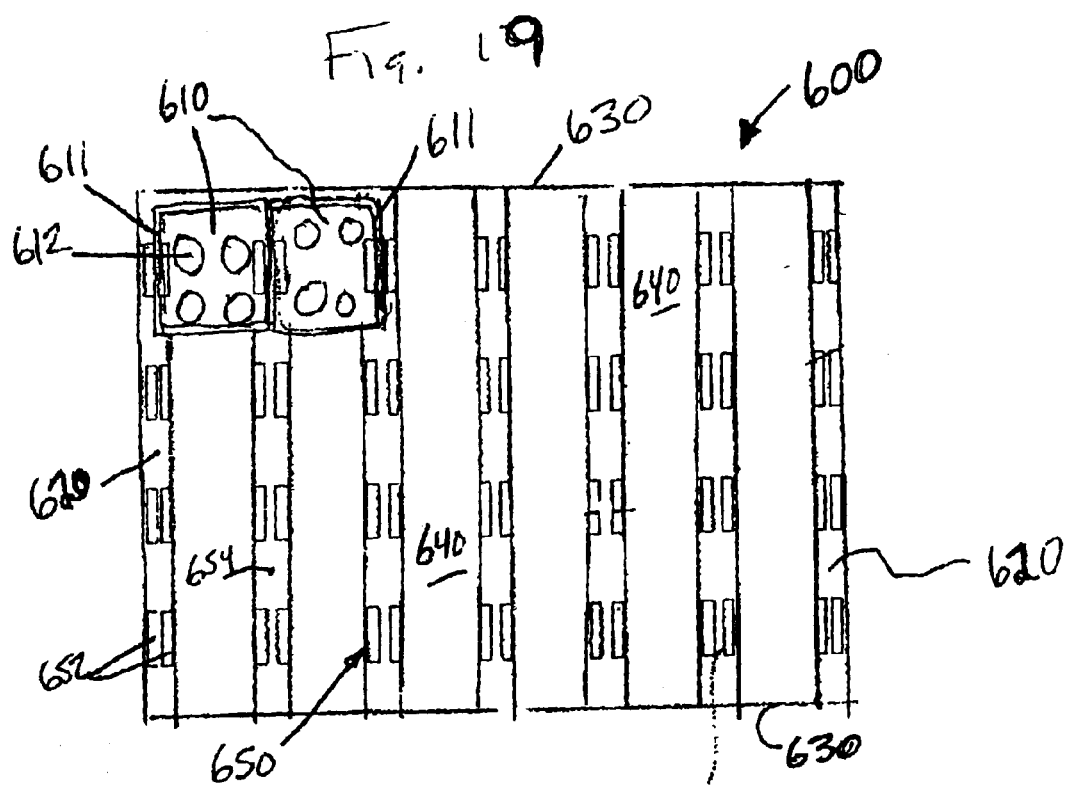

MICROFLUIDIC ARRAY DEVICES AND METHODS OF MANUFACTURE AND USES THEREOF

CROSS-REFERENCE TO RELATED APPLICATION

This application claims the benefit of U.S. patent application Ser. No. 60/341,069, filed Dec. 19, 2001, which is hereby incorporated by reference in its entirety.

TECHNICAL FIELD

The present invention relates to microfluidic devices, and more particularly, to microfluidic array devices that can be used to deliver one or more samples through one or more nozzles that are formed as part of the microfluidic array device. Exemplary manufacturing methods for fabrication of the microfluidic array devices are also disclosed as well as exemplary uses for the microfluidic array devices. For example, the microfluidic array device is suitable for operations designed for lab-on-a-chip functions including analysis of components in the sample fluid by means of optical spectrometry, mass spectrometry, etc.

BACKGROUND

There has been a growing interest in the development and manufacturing of microscale fluid systems for the acquisition of chemical and biochemical information and as a result of this effort, microfluidics is considered an enabling technology for providing low cost, high versatility devices to operations, such as combinatorial chemistry for drug lead discovery and large-scale protein profiling to name a few. Generally, a microfluidic device (which is also often referred to as a lab-on-a-chip device) is a planar device having one or more micron sized channels formed therein and can also include reservoirs, valves, flow switches, etc. The microfluidic features are designed to carry out complex laboratory functions, such as DNA sequencing.

In the absence of using microfluidic devices, the above processes and others are carried out in a manner that is very time intensive and thus, costly. For example, large-scale protein profiling is commonly carried out laboriously but pervasively in the biotechnological and pharmaceutical industries. One particular application of microfluidic devices is to provide micofluidic channels that represent the means to separate analytes in a mixture using techniques, such as capillary electrophoresis and liquid chromatography.

Microfluidic devices have traditionally been fabricated from substantially planar substrates with microfabrication techniques that have been borrowed from the electronics industry, such as photolithography, chemical etching, and laser ablation techniques. When constructing the microfluidic devices in this manner, the microfluidic channels that are formed lie parallel to the surface of one planar surface of the substrate, and the channel is sealed by bonding a second planar substrate to the planar substrate containing the channel. The techniques for detecting materials, such as analytes, that are disposed in the microfluidic channels have for the most part been mainly optical techniques. Fluid transport in the microfluidic devices traditionally entails using electroosmotic, electrokinetic and/or pressure-driven motions of liquid and particles as the means for fluidly transporting such materials.

While the stacking of multiple layers of planar substrates to form a microfluidic structure having layered microfluidic channels is possible in terms of its fabrication, the prevailing detection technology (optically based detection technology) limits the practicality of fabricating such a structure since parallel operation of multiple layers of the planar substrates containing multiple microfluidic separation channels is not practical due to each microfluidic separation channel requiring its own light source and detector.

One detection technology that is fast becoming the detection technique of choice in the biotechnology and pharmaceutical industries is mass spectrometry (MS). Mass spectrometry provides more chemical information about the material being tested (e.g., analytes) than other single detection techniques. For example, molecular weight and even chemical composition of the analytes from small drug candidate molecules to large protein molecules can be successfully analyzed by mass spectrometry (MS) and its related technique that is referred to as MS-MS. In MS-MS, a molecule is ionized and analyzed for molecular weight in the first stage of the mass spectrometer, and then the same molecular ion, called the "parent", is fragmented inside the mass spectrometer to produce "daughter" ions that are further analyzed to give the chemical composition of the parent molecule.

While some progress has been made to interface microfluidic devices with a mass spectrometer, there are still several shortcomings that must be overcome in order to make this interfacing process more practical. For example, one technique that has been discussed involves drilling a small hole, large enough to accommodate a glass or quartz capillary, into the end of the microfluidic channel that is formed by glass substrates and a glass or quartz capillary is then inserted into the drilled hole to act as a nozzle for electrospray ionization. This approach is laborious and is impractical for high throughput operations where many such holes have to be drilled sequentially into the substrates.

In another technique that has been disclosed, a protrusion termed "electropipette" extends from the edge of the substantially planar substrate. The microfluidic channel in this extended region is formed by two planar substrates as in the microfluidic channels that are formed in the rest of the microfluidic device. The outside dimensions of the tip structure include a thickness that is equal to the thickness of the two planar substrates. It has also been disclosed to fabricate an array of nozzles using microfabrication techniques, such as deep ion reactive etching on a silicon wafer. However, the use of silicon wafers as the substrates greatly limits the ability to individually activate each nozzle because of the potential of dielectric breakdown caused by the high voltage applied to the nozzle to create the electrospray conditions, and the volume behind the nozzle made by deep ion reactive etching is extremely difficult to be accessed by conventional means of liquid handling equipment. Integrating this silicon-based nozzle array to microfluidic devices, which are typically made of glass or polymers, is also extremely difficult. The cost of fabricating the nozzles on silicon is also very high.

While injection molding has been discussed as a process for forming microfluidic devices, there are a number of limitations that have equally been associated with such discussion of injection moldable microfluidic devices. For example, it has heretofore been discussed that there are limitations on what size dimensions can be formed when an injection molding process is used to form the microfluidic features. Prior to the present applicant, there was a lack of appreciation and understanding that an injection molding process can be used to form a microfluidic device having microfluidic features with dimensions less than 100 $\mu$m. As a result, the use of injection molding as a fabrication process was limited since many microfluidic applications require the microfluidic device to have microfluidic features (e.g., channels) that have dimensions less than 100 µm and more particularly, less than 50 µm.

It would therefore be desirable to provide microfluidic devices, especially microfluidic array devices incorporating nozzles, that overcome the deficiencies of the traditional microfluidic devices and more particularly, the deficiencies that are related to the techniques for fabricating these devices and also to the use of such devices.

SUMMARY OF THE INVENTION

The present application generally relates to microfluidic devices. According to one aspect, a microfluidic device is provided and includes a body having a first surface and an opposing second surface. At least one channel is formed through the body such that the channel extends from the first surface to the opposing second surface with the channel having an open reservoir section formed at the first surface. The microfluidic device further includes at least one nozzle that is disposed along the second surface. The nozzle is in fluid communication with one channel such that each channel terminates in a nozzle opening that is formed as part of the nozzle tip. Unlike traditional microfluidic devices, the exemplary microfluidic device has one or more channels that are open at each end and are formed substantially perpendicular to both the first surface and the second surface where the nozzle is formed.

According to another aspect, the nozzle is conically shaped with the channel extending therethrough and terminating at the nozzle opening. In one exemplary embodiment, the nozzle opening has a diameter equal to or less than 100 µm, preferably equal to or less than 50 µm and more preferably, equal to or less than 20 µm; and an outside diameter of the nozzle, as measured at a tip portion thereof, is less than about 150 µm and preferably is equal to or less than about 100 µm, and more preferably equal to or less than 50 µm. For electrospray type applications, a conductive region is formed on the nozzle, preferably at a tip portion thereof, to permit a voltage to be applied to the tip portion of the nozzle. As the sample fluid is discharged from the nozzle, the electric field that is created by the conductive region serves to vaporize and ionize the sample and form a fine mist containing the sample. This fine mist can then be injected into an inlet port of an analytical instrument, such as a mass spectrometer, to detect and analyze components of the sample and obtain certain information about the components.

In another aspect of the present application, the microfluidic nozzle array device is formed by an injection molding process that permits the microfluidic nozzle array device to have the above dimensions. A mold is first fabricated with the mold being a negative impression of the channel architecture and nozzle array that are formed as part of the microfluidic nozzle array device. Preferably, the mold is made of a metal material and with at least some portions of the mold being polished to a high degree of finish, i.e., a mirror finish. More specifically, the polishing of a conical portion of the mold that is used to form the nozzle results in the nozzle having a very smooth outer surface and also facilitates the flow of an injected polymer within this nozzle region, thereby increasing the accuracy and the efficiency of the injection molding process. A suitable polymeric material is injected into the mold and is then cured to form the injection molded microfluidic nozzle array device. After the device has sufficiently cooled, the microfluidic nozzle array device is then removed from the mold.

The exemplary microfluidic nozzle array devices disclosed herein can be used in a number of different applications. For example, the device is particularly well suited for operations designed for lab-on-a-chip functions including the detection of components in the sample fluid by means of UV, visible light and by means of mass spectrometry. Moreover, it will be appreciated that the microfluidic nozzle array device can be used in a wide range of other applications in which similar conventional microfluidic devices have or could be used. For example, the microfluidic nozzle array device can be used for spotting DNA or protein array on a substrate instead of using the conventional capillary wicking methods that are now used. The microfluidic nozzle array device can also be used for spotting the plate for matrix-assisted laser desorption ionization (MALDI), replacing the pipette and capillary spotting methods. In addition, the microfluidic nozzle array device can be in other spray or spotting type applications where it is desired to produce a fine stream of sample fluid.

These and other features and advantages of the exemplary embodiments disclosed herein will be readily apparent from the following detailed description taken in conjunction with the accompanying drawings, wherein like reference characters represent like elements.

BRIEF DESCRIPTION OF THE DRAWING FIGURES

The foregoing and other features of the exemplary embodiments will be more readily apparent from the following detailed description and drawings of illustrative embodiments that are not necessarily drawn to show exact likeness or necessarily to scale in which:

FIG. 11 is a cross-sectional view of one microfluidic channel/nozzle arrangement wherein a sample reservoir is sealed by a member having a polymeric cover sheet which is insertable and movable within the reservoir for discharging the sample through a nozzle opening;

FIG. 12 is a cross-sectional view of one microfluidic channel/nozzle arrangement wherein a sample reservoir is sealed by a member having an elastic sealing base which is insertable and movable within the reservoir for discharging the sample through a nozzle opening;

FIG. 13 is a cross-sectional view of one microfluidic channel/nozzle arrangement where a sample reservoir is sealed by a piston device having a bore extending therethrough for injecting a fluid into the sample reservoir to cause the sample to be discharged through a nozzle opening;

FIG. 19 is a top plan view of a retaining base according to another embodiment for releasably holding a number of microfluidic nozzle subunit structures.

DETAILED DESCRIPTION OF PREFERRED EMBODIMENTS

Figure 1:
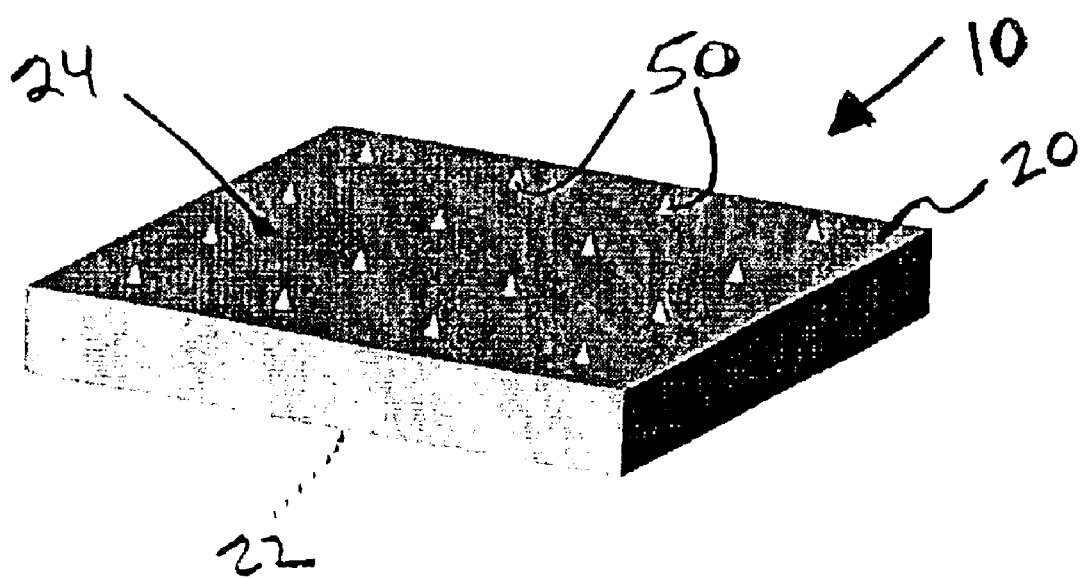
FIG. 1 is a top perspective view of a microfluidic device having an array of nozzles incorporated therein according to a first exemplary embodiment.
Figure 2:
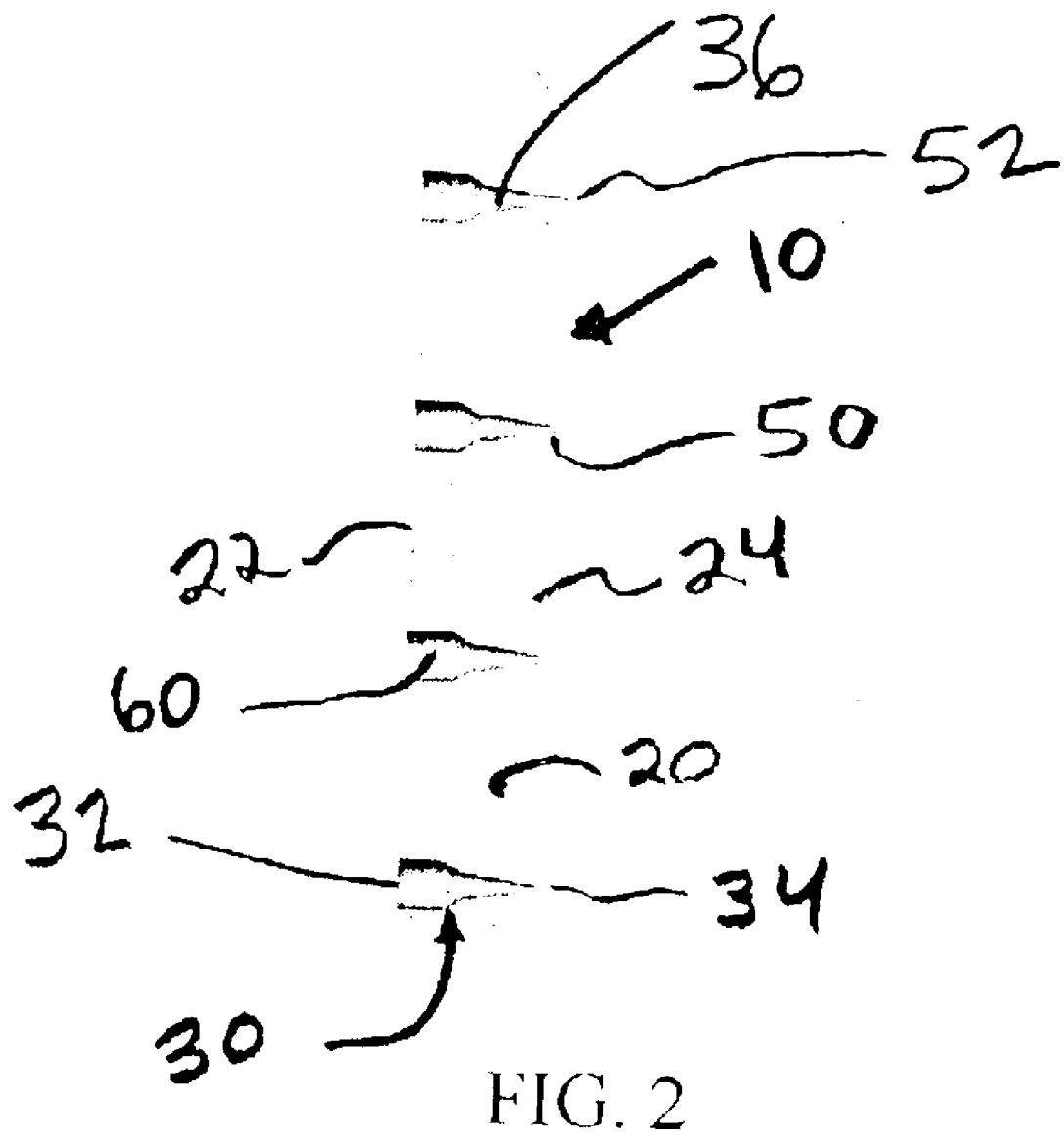
FIG. 2 is a cross-sectional view taken along the line 2—2 of FIG. 1.

Referring first to FIGS. 1–2 in which an exemplary microfluidic device 10 according to one embodiment is illustrated. The microfluidic device 10 has a substrate body 20 that is formed of a polymeric material, as will be described in greater detail hereinafter, and has at least one microfluidic channel 30 that is formed in the substrate body 20. More specifically, the substrate body 20 has a first surface 22 and an opposing second surface 24 with the microfluidic channel 30 being formed between the first and second surfaces 22, 24 such that the microfluidic channel 30 extends the complete thickness of the substrate body 20. The microfluidic channel 30 is thus open at both a first end 32 at the first surface 22 and a second end 34 at the second surface 24. The second end 34 of the microfluidic channel 30 is formed in a protrusion 50 that is formed on the second surface 24 of the substrate body 20. According to one exemplary embodiment, the protrusion 50 has a tapered shape (inward taper) such that it forms a generally conical structure with the open second end 34 preferably being formed at an apex of the conical structure. The tapered protrusion 50 serves as a nozzle that delivers a sample (i.e., a liquid) that is loaded into the microfluidic device 10.

It will be appreciated that in contrast to traditional microfluidic devices, the microfluidic channel 30 is formed in a perpendicular manner in the substrate body 20 in that the microfluidic channel 30 is preferably formed so that it is substantially perpendicular to the first and second surfaces 22, 24 of the substrate body 20. As illustrated, a predetermined number of microfluidic channels 30 and nozzles 50 can be formed in one substrate body 20. The microfluidic channels 30 can be arranged according to any number of different patterns. For example and as illustrated in the exemplary embodiment of FIGS. 1 and 2, which illustrate a preferred arrangement, a plurality of microfluidic channels/nozzles are arranged in regular arrays having spacing that is identical to or similar to spacing of microtiter plates. For example, if 96 microfluidic channels/nozzles are desired, then the 96 microfluidic channels/nozzles are arranged in an 8×12 grid with spacing of about 9 mm between each microfluidic channel/nozzle structure. For a 384 microtiter array, the microfluidic channels/nozzles are placed in a 16×24 grid with spacing of about 4.5 mm. While not entirely to scale, FIG. 2 generally illustrates a section of a microfluidic channel/nozzle array having spacing of about 4.5 mm.

According to the present exemplary embodiments, each nozzle 50 is constructed so that its dimensions are measured in microns. The specific configurations of the nozzle 50 and the microfluidic channel 30 are best shown in FIG. 2. As illustrated, the first end 32 of the microfluidic channel 30 is in the form of a reservoir 60 (i.e., an annular cavity) that tapers inwardly to an intermediate channel section 36. The intermediate channel section 36 also has a tapered construction in that it tapers inwardly toward the second end 34 and the nozzle 50 formed at the second surface 24 of the substrate body 20. Thus, the dimensions of the microfluidic channel 30 are greatest at the first end 32, where the reservoir is formed, and are at a minimum at the second end 34 at a tip portion 52 of the nozzle 50. According to one exemplary embodiment, the open second end 34 of the microfluidic channel 30 formed in nozzle 50 has an inside diameter of about 100 $\mu$m or less, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m. The inside diameter of the microfluidic channel 30 opens gradually in a direction away from the nozzle 50 to about several hundred $\mu$m as the microfluidic channel 30 traverses through the thickness of the substrate body 20 and eventually the microfluidic channel 30 is formed to a diameter of about 1 mm to define the reservoir at the first end 32. The length of the microfluidic channel 30 can be tailored to a given application depending upon a number of factors, such as the desired volume of the reservoir defined at first end 32 and also the thickness of the substrate body 20. According to one exemplary embodiment, the microfluidic channel 30 has a length of about 3 mm or greater. However, the aforementioned dimensions are merely recited to illustrate one exemplary embodiment and it will be understood that the microfluidic device 10 can be fabricated to have other dimensions.

The volume of the reservoir 60 should be such that it can hold an amount of sample material that is typically used in the applications that the microfluidic devices are designed for. For example, the sample volume that is used is from sub-microliter up to 10 microliters for mass spectrometer analysis using electrospray. As will be described in greater detail hereinafter, the sample material is held in the reservoir 60 and is then transported within the microfluidic channel 30 to the nozzle 50 where the sample materials are finally discharged through the open second end 34. The outside diameter of the protruding nozzle 50 also accordingly increases in a direction away from the tip portion 52 thereof. By forming the reservoir 60 or input port at the first surface 22 opposite to the second surface 24, where the nozzle 50 is formed, a sample can easily be fed into the microfluidic channel 30 by injecting or otherwise disposing the sample into one or more reservoirs 50 and then transporting the sample through the associated microfluidic channel 30 using techniques described in greater detail hereinafter.

Figure 3:
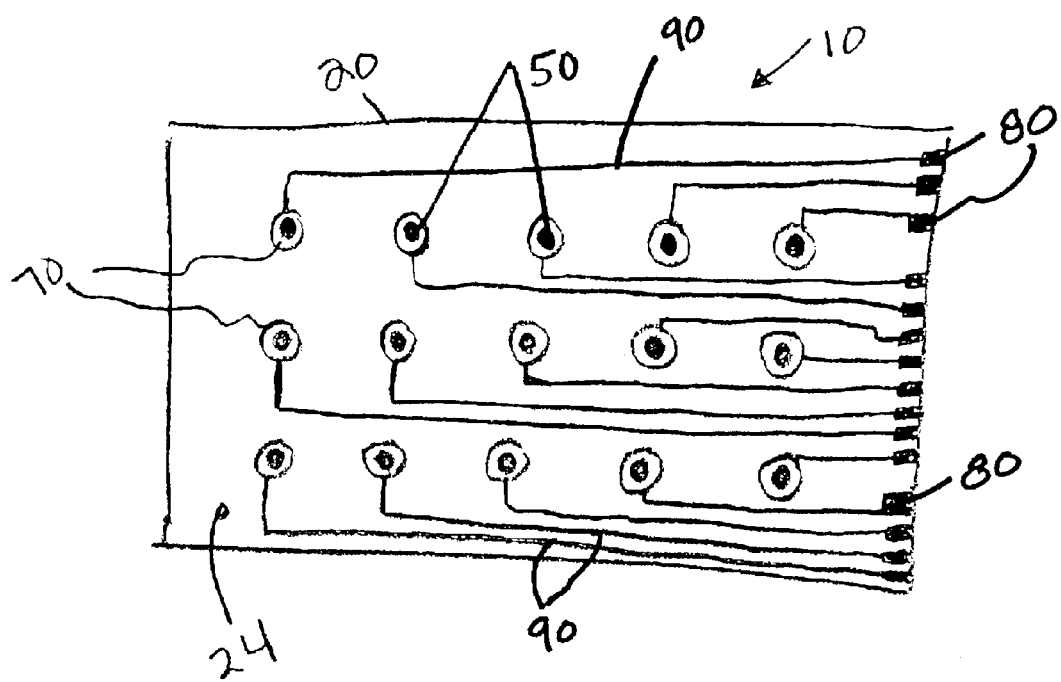
FIG. 3 is a top plan view of the microfluidic device according to FIG. 1 illustrating placement of electrodes around the nozzles and the connections between the electrodes and electrical contacts formed at one edge of the microfluidic device.

Turning now to FIG. 3, the microfluidic device 10 can be fabricated so that it finds particular utility as a means for electrospray ionization of analytes for mass spectrometer analysis. Electrospray is achieved by subjecting the nozzle 50 to a voltage so that liquid and analytes (the "sample") emerge to a high electric field. For this particular application, the microfluidic device 10 includes a conductive region 70 formed on at least a portion of the nozzle 50 and optionally, the conductive region can extend onto the second surface 24. For example, the area around each nozzle 50 up to the extreme end of the nozzle 50 is metallized by evaporation techniques, printing techniques, or other suitable techniques known in the art to form the conductive region 70. Because the nozzle 50 in the illustrated embodiment has a conical shape, the conductive region 70 takes the form of a ring-shaped metal layer with the nozzle 50 being in the center thereof. The thickness of the conductive region 70 can vary depending upon the precise application; however, the conductive region 70 should have a sufficient thickness so that when an electric voltage is applied to the conductive region 70, the sample material (i.e., a liquid) within the microfluidic channel vaporizes and therefore can be used in electrospray or nanospray applications, such as electrospray ionization of analytes for a mass spectrometer. The microfluidic device 10, in this example, provides a low cost, disposable electrospray interface capable of nanospray. This device can be fabricated to accommodate more than one sample input in order to multiplex several separation instruments to a single mass spectrometer.

Each of the conductive regions 70 formed around the nozzles 50 is connected to one or more electrical contacts 80 formed at one edge of the substrate body 20. More specifically, the electrical contacts 80 are preferably in the form of conductive pads (i.e., metallized tabs) that are formed on the second surface 24 of the substrate body 20. FIG. 3 shows one exemplary method of electrically connecting the conductive regions 70 with the electrical contacts 80. In this exemplary arrangement, one conductive region 70 is electrically connected via an electrical pathway 90 to one electrical contact 80. The electrical pathway 90 simply provides an electrical pathway between the conductive region 70 and the electrical contact 80 and is therefore formed of a conductive material (e.g., a metal). For example, the electrical pathway 90 can be in the form of a thin conductive film. By reducing the outside diameter of the tip portion 52 of the nozzle 50 (e.g., to about 50 $\mu$m to 80 $\mu$m), the voltage required to generate the spray is lowered. According to one exemplary embodiment, the voltage used to form the spray is about 5–6 KV for a tip portion 52 having an outside diameter from about 50 $\mu$m to 80 $\mu$m. It will be appreciated that larger sized outside diameters can be used; however, this will require a greater voltage to be applied to the nozzle 50 in order to form a spray.

It will be appreciated that more than one conductive region 70 can be electrically attached to one electrical contact 80 using separate electrical pathways 90 or using a network of electrical pathways or a complete metal film. However, in this embodiment, when an electric voltage is applied to the one electrical contact 80, the electric voltage is applied to each of the conductive regions 70 that is electrically connected to the one electrical contact 80. Thus, the electric voltage can not be selectively delivered to individual nozzles 50 in this particular embodiment.

Figure 4:
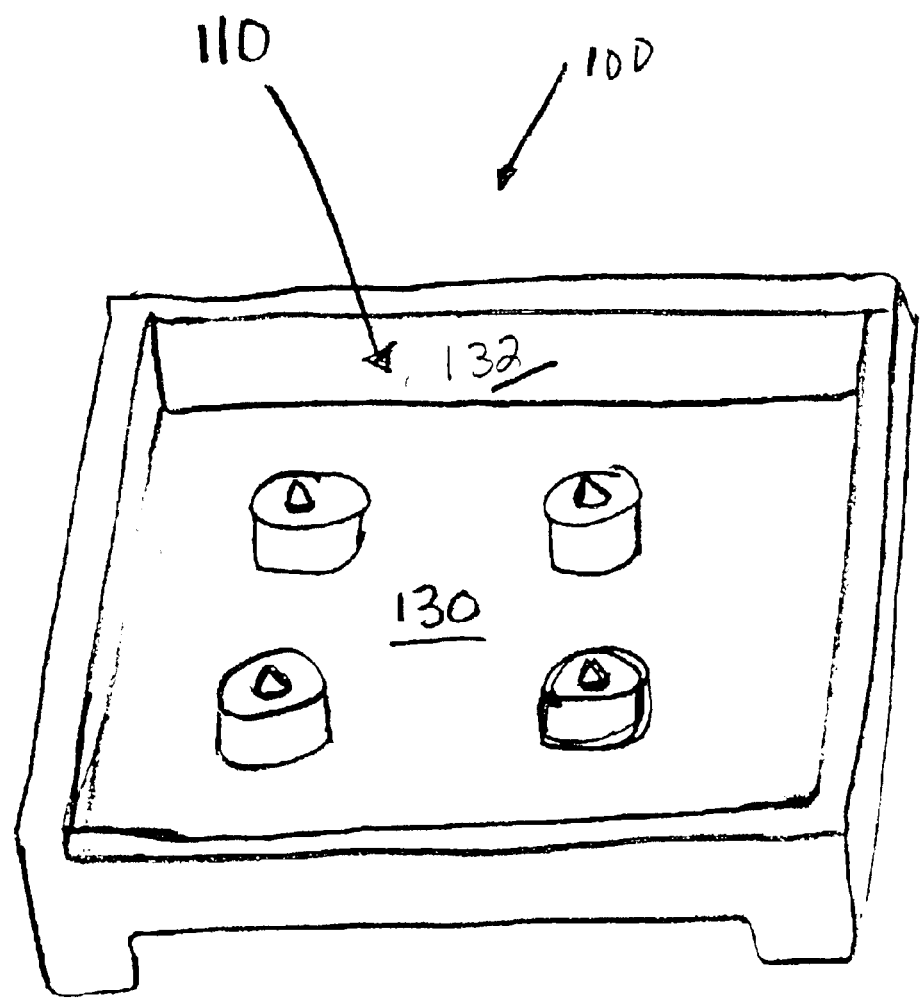
FIG. 4 is a top perspective view of a microfluidic device having an array of nozzles incorporated therein according to a second exemplary embodiment.
Figure 5:
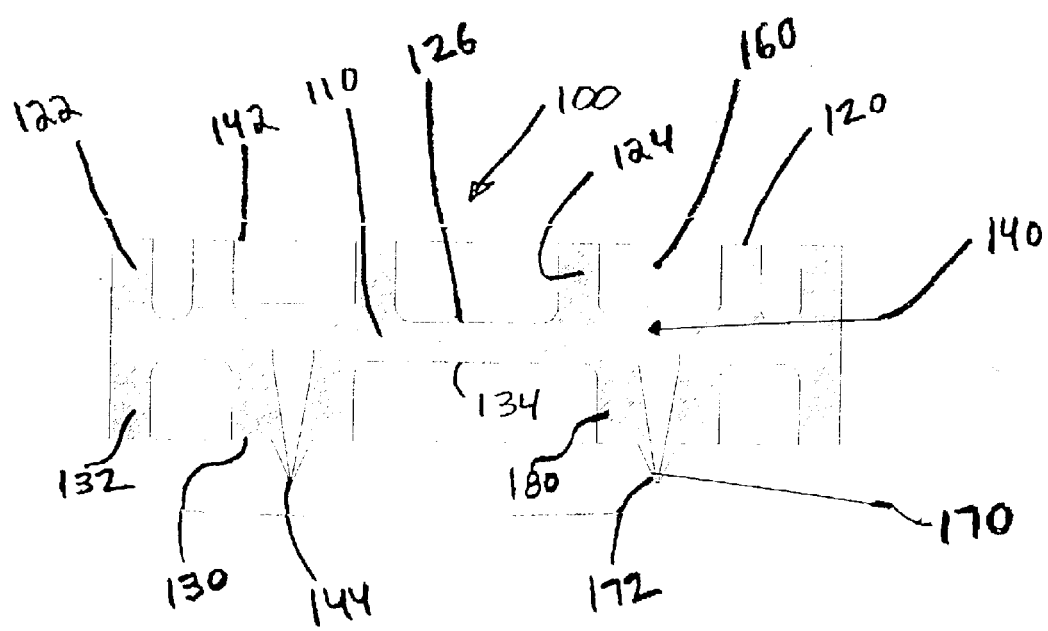
FIG. 5 is a cross-sectional view of the microfluidic device according to FIG. 4.

Now referring to FIGS. 4–5, an exemplary microfluidic device 100 according to a second embodiment is illustrated. The microfluidic device 100 is similar in some respects to the microfluidic device 10 of FIGS. 1–3. The microfluidic device 100 includes a substrate body 110 that is formed of a polymeric material and includes a first face 120 and a second opposing face 130. Unlike the embodiment illustrated in FIGS. 1–3, the first and second faces 120, 130 are not substantially planar surfaces but rather are non-planar in nature due to each of the faces 120, 130 having a number of recesses and protrusions formed therein.

The microfluidic device 100 has at least one microfluidic channel 140 formed therein between the first face 120 and the second face 130 such that the microfluidic channel 140 extends completely through a thickness of the substrate body 110 from the first face 120 to the second face 130. The microfluidic channel 140 is thus open at both a first end 142 at the first face 120 and at a second end 144 at the second face 130. The first face 120 includes a first perimeter wall 122 that extends around a perimeter of the microfluidic device 100 at the first face 120 thereof. In the exemplary embodiment, the microfluidic device 100 is generally square shaped; however, this is merely one exemplary shape for the microfluidic device 100 as the microfluidic device 100 can assume any number of different shapes. Within the boundary of the first perimeter wall 122, one or more reservoir walls 124 are formed with the number of reservoir walls 124 equal to the number of microfluidic channels 140 formed in the substrate body 110. Each reservoir wall 124 partially defines a reservoir 160 that is designed to hold a sample material and the reservoir wall 124 therefore also defines the first end 142 of the microfluidic channel 140. Both the first perimeter wall 122 and the one or more reservoir walls 124 extend above a generally planar surface 126 (i.e., a floor) of the first face 120 in this embodiment. A substantial portion of reservoir 160, which is defined at the first end 142 of the microfluidic device 140, is therefore formed above the planar surface 126.

The second end 144 of the microfluidic channel 140 is formed in a protrusion 170 that extends outwardly from the second face 130. As with the prior embodiment, the protrusion 170 preferably has a tapered shape (inward taper) such that it forms a generally conical structure with the open second end 144 being formed at an apex of the conical structure. The tapered protrusion 170 therefore acts as a nozzle that can discharge a sample that is loaded into the microfluidic channel 140 (e.g., in the reservoir 160). The nozzle 170 is therefore part of the microfluidic channel structure since the microfluidic channel 140 is formed therethrough and terminates at the nozzle opening.

The second face 130 is also not substantially planar but rather includes a second perimeter wall 132 that extends at least partially around a perimeter of the second face 130. The second face 130 does contain a floor 134 that is substantially planar. Between the second perimeter wall 132, one or more nozzle base sections 180 are formed with the number of nozzle base sections 180 being equal to the number of microfluidic channels 140. The nozzle base sections 180 are integrally formed with and extend outwardly from the floor 134 and in the illustrated embodiment, each nozzle base section 180 has a generally annular shape. However, the shape of the nozzle base section 180 is not limited to an annular shape and instead can have any number of shapes, including a conical shape or a tapered shape or any other regular or irregular shape. According to one embodiment, a plane that contains the upper edge of the second perimeter wall 132 generally cuts through the interface between the nozzle base section 180 and the nozzle 170. The nozzle 170 therefore extends beyond the upper edge of the second perimeter wall 132. According to one embodiment, the diameter of the reservoir 160 is about equal to the outside diameter of the nozzle base section 180; and therefore, an outside diameter of the reservoir wall 124 is greater than the outside diameter of the nozzle base section 180.

The specific configurations of the nozzle 170 and the microfluidic channel 140 are best shown in FIG. 5. As illustrated, the first end 142 of the microfluidic channel 140 is in the form of the reservoir 160. A distal end of the reservoir 160 has an inwardly tapered construction that leads to an intermediate channel section 146. A substantial length of the intermediate channel section 146 is formed in the nozzle base section 180. The intermediate channel section 146 also has a tapered construction in that it tapers inwardly toward the nozzle 170 defined at the second end 144 of the microfluidic channel 140. Thus, the dimensions of the microfluidic channel 140 are greatest at the first end 142 and are at a minimum at a tip portion 172 of the nozzle 170. In one embodiment, the microfluidic feature formed in the device 100 beginning with the reservoir 160 and terminating with the nozzle 170 is generally cylindrical in shape along its length. According to one exemplary embodiment, the open second end 144 of the microfluidic channel 140 formed at the tip portion 172 has an inside diameter equal to or less than 100 $\mu$m, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m. The inside diameter of the microfluidic channel 140 varies along its length due to its tapered construction. For example, the inside diameter of the microfluidic channel 140 opens gradually in a direction away from the nozzle 170 to about several hundred $\mu$m as the microfluidic channel 140 traverses through the thickness of the substrate body 110 and eventually, the microfluidic channel 140 is formed to a diameter of about 1.5 mm to define the reservoir 160. The length of the microfluidic channel 140 can be tailored in view of the construction details of the microfluidic device 100 and the potential applications of the device 100. In one example, the length of the microfluidic channel 140 is about 3 mm; however, this will vary depending upon the thickness of the device 100, the amount of sample that is to be loaded into the device, etc.

As with the first embodiment, the microfluidic channel 140 is formed in a substantially perpendicular manner in the substrate body 110 since the microfluidic channel 140 is formed substantially perpendicular to both the first and second faces 120, 130. While, the nozzle 170 extends beyond a plane containing the distal edge of the second perimeter wall 132, the distal end of the reservoir wall 124 preferably lies within the same plane that contains the distal edge of the first perimeter wall 122. This orientation permits a cover (e.g., thin polymeric cover sheet) or seal member to be disposed across the distal edge of the first perimeter wall 122 and the distal ends of the reservoir wall 124 to effectively seal the sample material within the reservoir 160, as will be described hereinafter.

One will appreciate that one of the advantages of the device 100 is that it is formed as a one piece construction in contrast to conventional devices which have multiple layers bonded together. In these conventional devices, the microfluidic channel is closed by the bonding of one layer over another layer. In other words, two separate layers are needed to define the complete channel. Because the present device 100 is injection-molded, separate bonded layers are not required.

It will be understood that the present configurations that are illustrated herein with reference to FIGS. 1–5 are merely exemplary in nature and are intended to merely convey exemplary embodiments. Various modifications can be performed to the microfluidic devices depending upon a number of different considerations, including manufacturing considerations. For example, the nozzle structures do not necessarily have to have conical shapes; however, for ease of manufacturing, a conical shape or the like is generally preferred.

According to another aspect of the present application, various manufacturing methods are disclosed herein for manufacturing the microfluidic array devices illustrated in FIGS. 1–5. In general terms, exemplary manufacturing processes disclosed herein permit microfluidic nozzle array devices to be manufactured having microscale nozzle dimensions (e.g., a nozzle tip opening having a diameter equal to or less than 100 $\mu$m, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m) and also the present microfluidic array devices are particularly suited to inexpensive fabrication methods. More specifically, the microfluidic array devices of the present application can be manufactured by injection molding a suitable thermoplastic using conventional injection molding techniques. Suitable thermoplastics include polycyclic olefin polyethylene copolymers, poly methyl methacrylate (PMMA), polycarbonate, polyalkanes, polyacrylate polybutanol co-polymers, polystyrenes, and polyionomers, such as Surlyn® and Bynel®. Polycyclic olefin polyethylene co-polymers are particularly suitable for use in an injection molding process. Various grades of such polymers are commercially available from Ticona under the trade name Topas® (which is a polyethylene-polycyclic olefin co-polymer). Furthermore, polybutyl terephthalate (PBT) can be used, as well as polyamides, such as nylons of different grades (nylon 6-6, nylon, 6 nylon 6-12, etc.); polyoxymethylene (POM) and other acetyl resins; and other resins with melt viscosity comparable to PBT and other properties similar to the other suitable polymers disclosed herein. Generally, polymers that are suitable for use in the present injection molding process include those thermoplastic polymers with a relatively low melt viscosity and these polymers preferably also have a high chemical purity (preferably the polymers are without more than a few percent of particulate additives and are chemically inert). Other suitable polymers include thermoplastics blended with a lubricant (e.g., liquid crystalline polymers) added to help the flow and therefore this additive acts as a processing aid and other liquid crystalline polymers containing polymers such as Zenite® (DuPont Company) and the like can be used and polymers (both commercially available and non-commercially available) that have high chemical purity, high chemical resistivity and thermal stability are also suitable. In some applications, injection-moldable elastomers may also be suitable.

In order to manufacture the present microfluidic array devices using injection molding techniques, a mold or mold insert must first be fabricated. The following description of the mold is merely exemplary for one type of mold construction which is oversimplified in terms of its construction in order to illustrate certain details of overall molding process. However, one of skill in the art will appreciate that the mold structure is readily changeable and is dictated by the desired construction of the microfluidic device and more particularly, the desired construction of the microfluidic channels based on the shape, dimensions and other properties thereof.

The mold typically is formed of several parts that mate with one another to form an assembled mold. The mold or mold insert is typically formed as a negative impression of whatever channel architecture or device features are desired in the microfluidic array device. A polymeric material is injected into the mold and then the polymeric material is cured to form the microfluidic array device which is then removed from the mold. Typically, the mold is formed of two mold dies that mate together in a sealed manner and therefore after the microfluidic device has been formed and is sufficiently cooled, the two mold dies are separated to permit access and removal of the microfluidic array device.

The mold (i.e., mold dies) or mold insert can be prepared from any number of materials that are suitable for such use, such as metal, silicon, quartz, sapphire and suitable polymeric materials; and forming the negative impression of the channel architecture can be achieved by techniques, such as photolithographic etching, stereolithographic etching, chemical etching, reactive ion etching, laser machining, rapid prototyping, ink-jet printing and electroformation. With electroformation, the mold or mold insert is formed as a negative impression of the channel architecture by electroforming metal and the metal mold is polished (preferably to a mirror finish).

For non-metallic molds for injection molding, the mold can be made of a flat, hard material such as Si wafers, glass wafers, quartz or sapphire. The microfluidic design features can be formed in the mold through photolithography, chemical etching, reactive ion etching or laser machining (which is commonly used in microfabrication facilities). In addition, some ceramics can be used to fabricate the mold or mold insert.

Molds can also be fabricated from a "rapid prototyping" technique involving conventional ink-jet printing of the design or direct lithography of resists, such as Su-8 or direct fabrication of the mold with photopolymers using stereolithography, direct 3-dimensional fabrication using polymers, and other similar or related techniques that use a variety of materials with polymers. A resulting polymer-based mold can be electroformed to obtain a metallic negative replica of the polymer-based mold. Metallic molds are particularly appropriate for injection molding of polymers that require the mold itself to be heated. One commonly used metal for electroforming is nickel, although other metals can also be used. The metallic electroformed mold is preferably polished to a high degree of finish or "mirror" finish before use as the mold for injection mold. This finish is comparable to the finish obtained with mechanical polishing of submicron to micron size abrasives (e.g., diamond particles). Electropolishing and other forms of polishing can also be used to obtain the same degree of finish. Additionally, the metallic mold surface should preferably be as planar and as parallel as the Si, glass, quartz, or sapphire wafers. In one exemplary embodiment, the metallic mold is polished to a highly polished finish by using 1 micron diamond particles to provide a finish that is close to a mirror-like finish.

Figure 6:
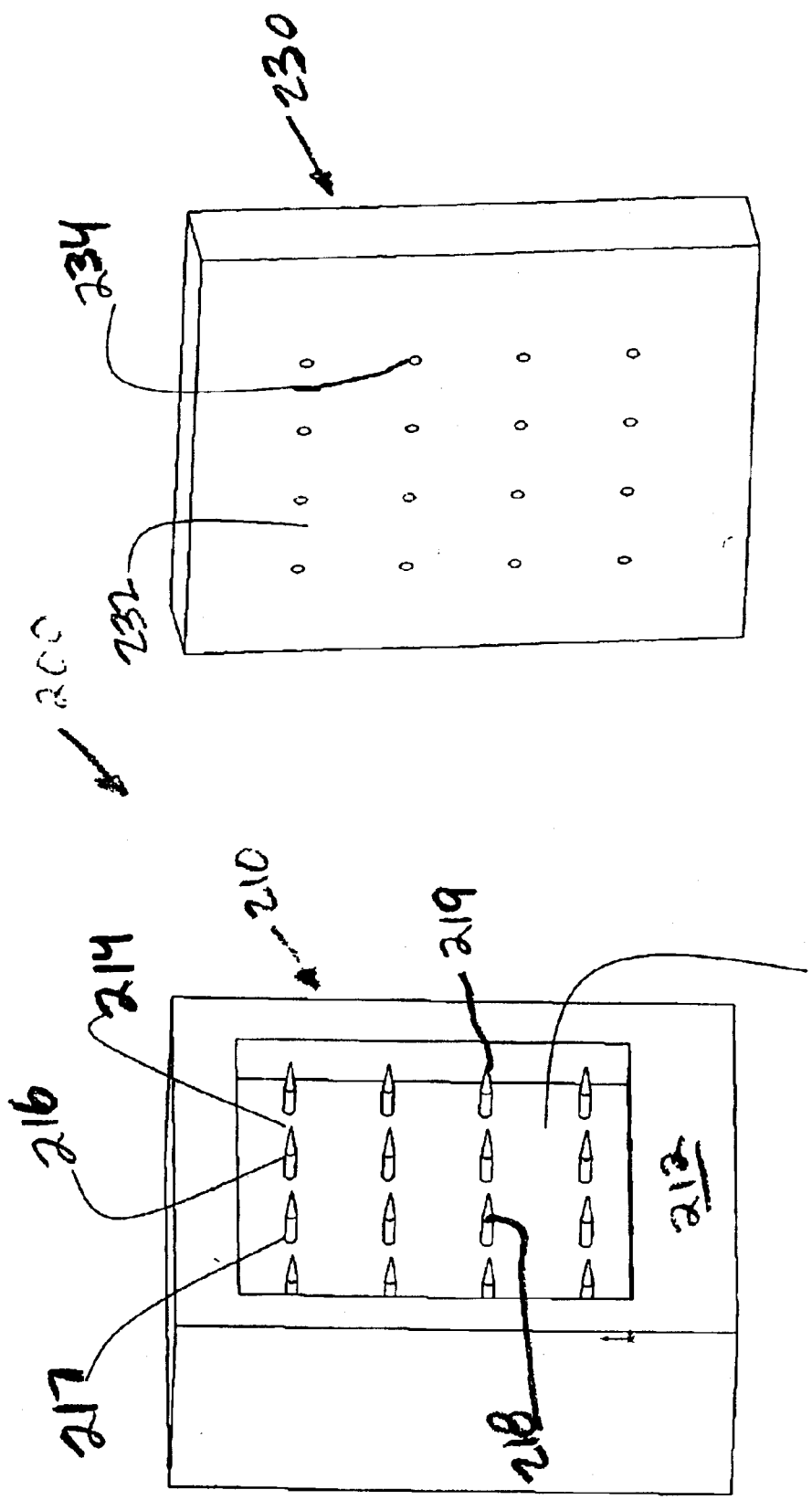
FIG. 6 is a perspective view of an exemplary mold used to manufacture the microfluidic device of FIG. 1.

The present applicant has discovered that injection molding techniques using a mold fabricated of hardened steel or other metals can be used to manufacture polymeric microfluidic devices having an array of micron sized nozzle structures with a nozzle opening having a diameter equal to or less than 100 $\mu$m, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m. FIG. 6 is a perspective view of a mold construction 200 that is constructed to injection mold a microfluidic nozzle array device, as shown in FIG. 1, having the aforementioned dimensions and properties. Once again, the mold 200 is formed as a negative impression of the microfluidic device that is to be formed. The mold 200 includes a first mold die or part 210 and a second mold die or part 230 that are constructed so that they are complementary to one another and mate with one another to form an injection mold assembly that is used to form a microfluidic nozzle array device, similar to device 10 illustrated in FIG. 1. The mold 200 is preferably formed by electric discharge machining (EDM).

The first mold die 210 has a first face 212 that includes a substantially planar surface. The first face 212 has a recessed section 214 formed therein. The recessed section 214 generally defines the outer peripheral shape of the microfluidic device and also the depth of the recessed section 214 defines the thickness of the microfluidic device (except in areas where the nozzles are formed). Because the microfluidic device typically has a square or rectangular shape, the shape of the recessed section 214 will be the same or similar. For example, the illustrated recessed section 214 is generally square shaped. The first mold die 210 also includes a plurality of upstanding contoured pins 216 that are spaced across a floor of the recessed section 214. The shape of each pin 216 directly corresponds to the shape of the microfluidic channel that will be formed when the mold 200 is closed and the polymeric material is injected. More specifically, a base section 217 of the pin 216 corresponds to the reservoir of the microfluidic channel; an intermediate section 218 corresponds to the intermediate section of the microfluidic channel and a conical tip section 219 of the pin 216 corresponds to the second end of the microfluidic channel that is formed in the tip portion of the nozzle. As a result, the dimensions of the pin 216 are greatest at the base section 217 and the pin 216 tapers inwardly to the conical tip section 219 thereof. The spacing of the pins 216 directly correlates to the spacing of the microfluidic channel/nozzle structure and therefore, the pins 216 are preferably spaced in arrays.

Figure 7:
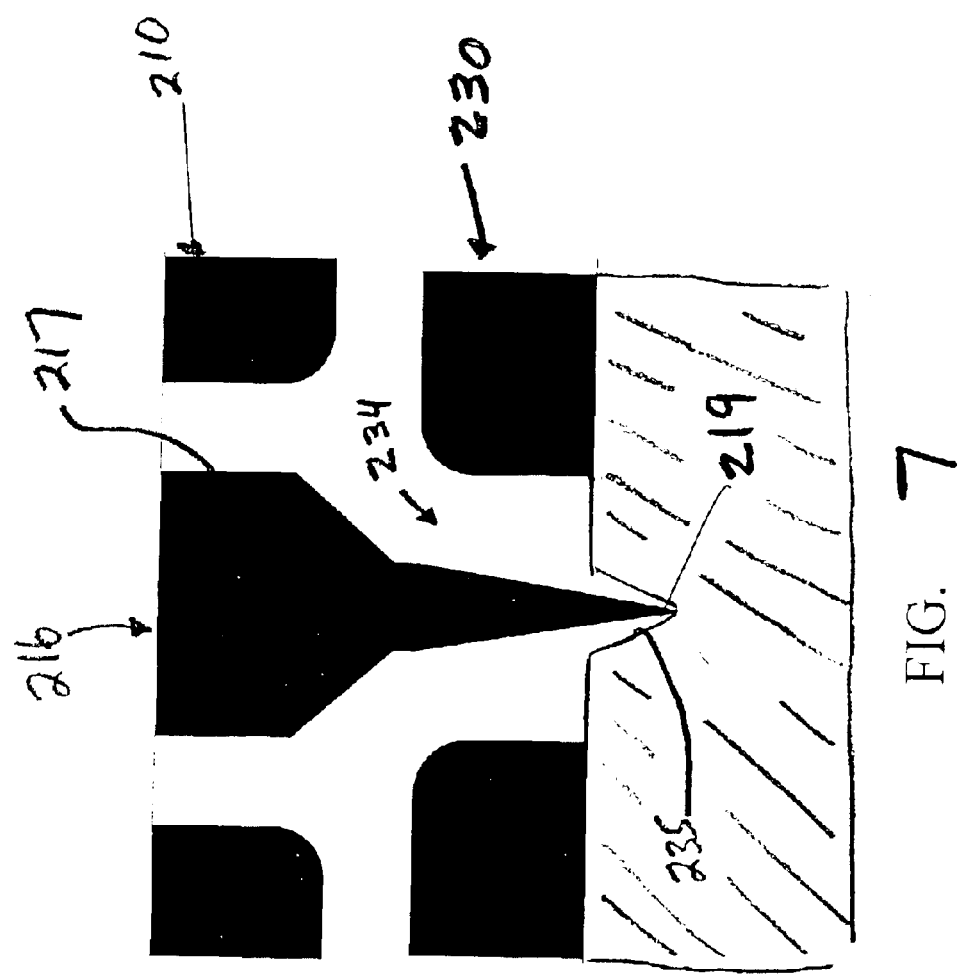
FIG. 7 is a cross-sectional view of first and second dies in a closed position that is used to manufacture the microfluidic device of FIG. 4.

Now referring to FIGS. 6–7, the second mold die 230 has a first face 232 that mates with the first face 212 of the first mold die 210. The first face 232 is substantially planar with the exception that a plurality of apertures 234 are formed in the second mold die 230. The apertures 234 are arranged according to a predetermined pattern that corresponds to the arrangement of the pins 216. The apertures 234 are sized so that they receive at least a portion of the conical tip sections 219 (about 500 $\mu$m in length in one embodiment) of the pins 216 when the first and second mold dies 210, 230 mate with one another. The apertures 234 are themselves contoured so that the apertures 234 taper inwardly with a lower portion 235 of each aperture 234 having a conical shape so as to form the conical nozzle of the microfluidic device. When the first and second molds 210, 230 mate together and the pins 216 are received in the apertures 234 according to one embodiment, the tip sections 219 of the pins 216 extend completely to the bottom of the apertures 234 and contact the body of the second die mold 210 that defines the closed ends of the apertures 234. The mold 200 of FIG. 6 is constructed to generally produce the microfluidic device 10 of FIG. 1.

FIG. 7 shows a cross-sectional view of a mold that is constructed to produce the microfluidic device 100 of FIG. 4. For purposes of ease of illustration and simplification, the reference numbers of FIG. 6 will be carried over to the description of FIGS. 7–9 since each of these illustrated molds includes first and second mold dies. It will be understood that the features that are formed as part of the first and second mold dies 210, 230 dictate the dimensions and shape of the features of the resulting microfluidic device.

It will therefore be appreciated that after the first and second mold dies 210, 230 are closed and any preparation steps that are necessary for the injection molding process are taken, the first faces of the first mold die 210 and the second mold die 220 seat against one another to effectively seal the recessed section 214 and the polymeric material (typically a resin) is then injected into the closed space that is defined in part by the recessed section 234. FIG. 7 shows a cross-sectional view of the first and second mold dies 210, 230 in a closed position with the tip section 219 of one pin 216 received within the aperture 234 and more specifically into the conically shaped lower portion 235 of the aperture 234. Because the first and second mold dies 210, 230 are negative impressions of the resultant microfluidic device, the microfluidic channel will take the form of the pin 216 and the nozzle of the microfluidic device is formed by the conically shaped lower portion 235. More precisely, the nozzle is formed by resin filling completely the space between the tip section 219 of pin 216 and the tip section of the conically shaped lower portion 235. As previously mentioned, in this embodiment, the tip section 219 of the pin 216 and the tip of the second mold die 230 that is formed in the conically lower shaped portion 235 are in contact with one another.

Mold 200 is intended to be used a number of times over a period of time to produce a great number of microfluidic devices and therefore the material that is selected for the fabrication of the mold 200 should be done so accordingly. In other words, a material should be selected that permits microscale features to be formed in the microfluidic device and also permits a great number of microfluidic devices to be formed using the mold 200. One material that is suitable for use in fabricating the mold 200 is hardened steel. With conventional machining technologies, such as metal turning and electric discharge machining (EDM), the dimensions of the tip section 219 of the pin 216, which forms the nozzle opening, can be limited. For example, the dimensions (i.e., the diameter and length) of the tip section 219 can be limited due to manufacturing considerations. The available manufacturing techniques permit the outside diameter of the nozzle to be formed to about 50 $\mu$m since it is possible to inject mold a resin into the space between the tip section 219 and the conically lower shaped portion 235. In some areas, this space is only on the order of about 15 $\mu$m due to the desired dimensions of the nozzle and the microfluidic channel.

While, the first mold die 210 is illustrated as having a square shape, it will be appreciated that the first mold die 210 can be formed to have any number of different shapes so long as the shapes of the first mold die 210 and the second mold die 230 permit these two components to mate with one another.

Figure 8:
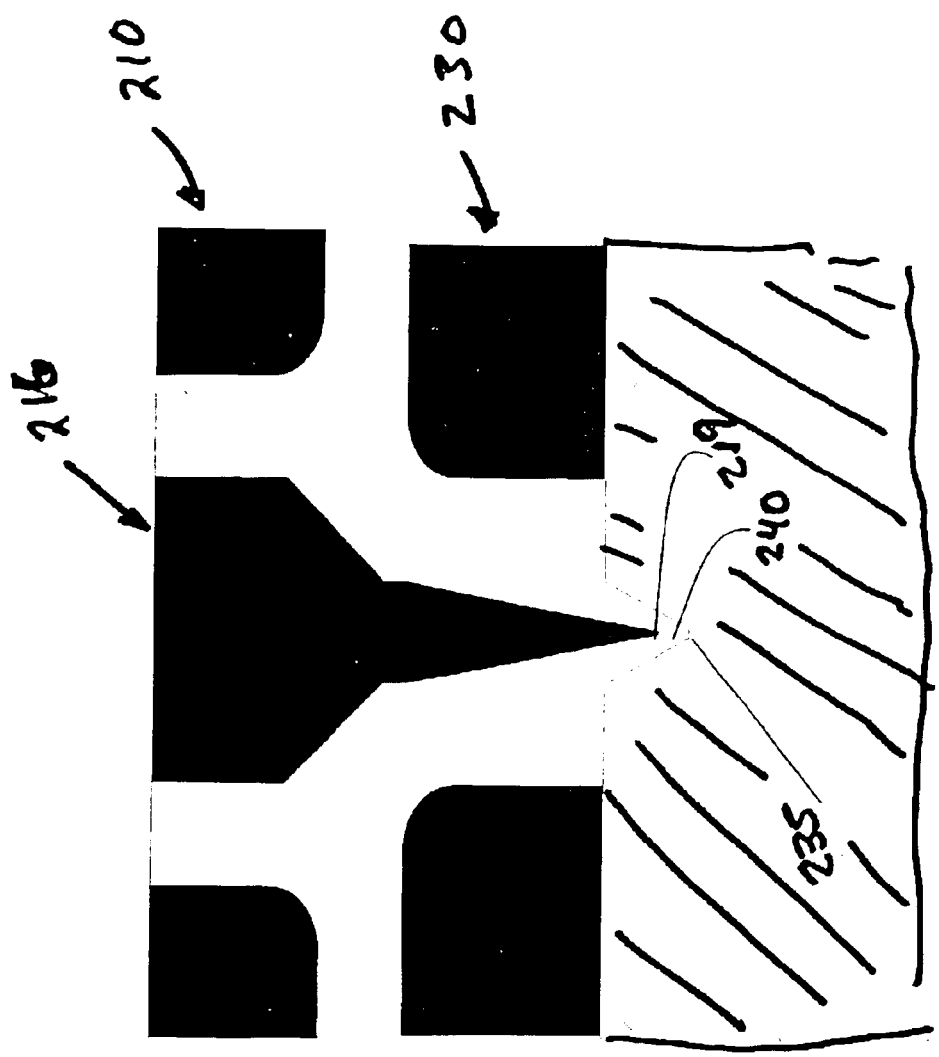
FIG. 8 is a cross-sectional view of first and second dies of the mold illustrating another embodiment where a gap is formed between a pin of the first mold and a nozzle forming feature of the second mold.

However, there are techniques available to injection mold a nozzle opening having smaller dimensions than the aforementioned dimensions. FIG. 8 illustrates one possible injection molding arrangement to accomplish this task and produce nozzles having nozzle openings that are even smaller than the tip section 219 of the pin 216. In FIG. 8, there is a gap 240 between the tip section 219 and the conically shaped lower portion 235 after the first and second mold dies 210, 230 have been assembled. When the polymeric material (e.g., a resin) is injected (in a molten state) into the conically shaped lower portion 235, the pressure of the injected resin is adjusted such that the resin does not fill the entire space in the gap 240 and an opening (space) remains at the tip of the resulting molded nozzle since sufficient pressure is not present to displace the resin to the lowermost section of portion 235. Using this technique, the diameter of the tip section 219 of the pin 216 can be greater than 20 $\mu$m since the opening of the nozzle and the outside diameter of the nozzle are no longer defined by the dimensions of the corresponding parts of mold but rather are defined by a combination of mold dimensions, gap dimension and injection pressure. In this manner, the pins 216 do not have to be manufactured to have a tip section 219 on the order of 20 $\mu$m in order to form a nozzle opening of the same dimension. Instead, the tip section 219 can have a diameter greater than the diameter of the nozzle opening that is ultimately formed in the nozzle as a result of the injection molding process.

Figure 9:
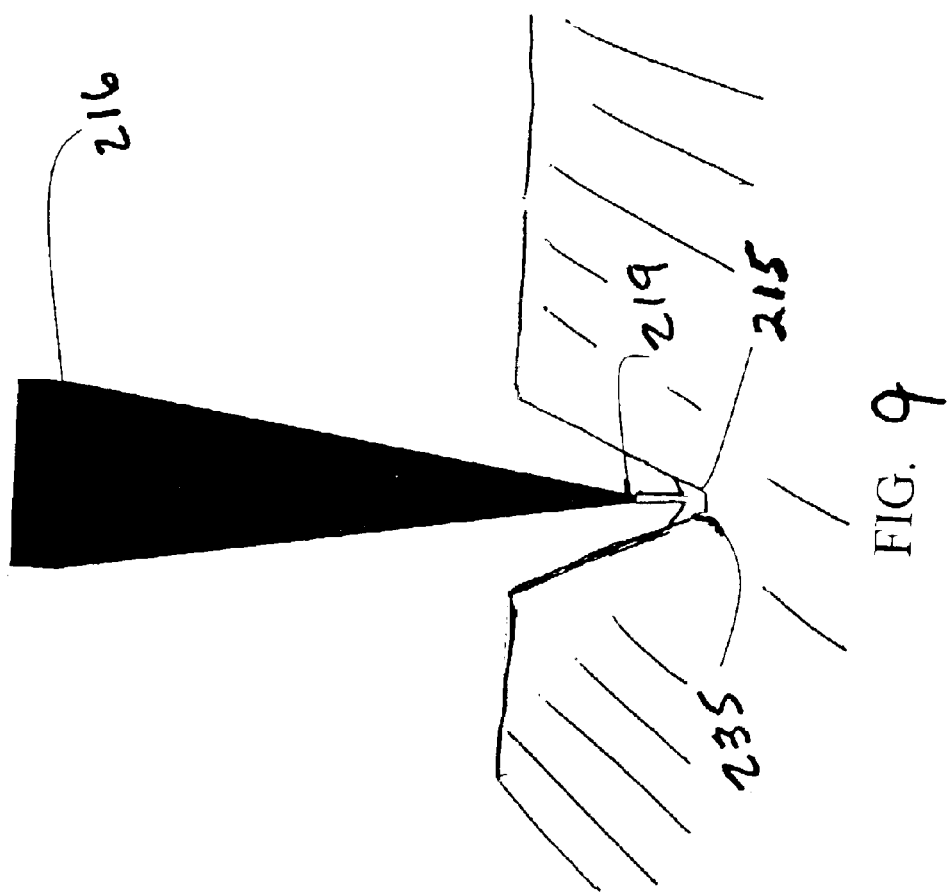
FIG. 9 is a cross-sectional view illustrating a mold arrangement for fabricating a micron sized nozzle opening.

FIG. 9 illustrates one exemplary method of overshooting the injected resin into the gap 240 formed between the tip section 219 and the tip of the conically shaped lower portion 235. The nozzle opening 215 is defined by pressure used to inject the molten resin and the dimensions of the gap 240. By controlling these parameters, the dimensions of the nozzle opening can be controlled.

Injection molding as a manufacturing technology for polymer parts is low-cost at high-volume production. However, there is considerable cost involved in the production of the mold itself, especially for a microfluidic nozzle design which has micron sized features and therefore is a demanding design in terms of producing a mold. If the microfluidic nozzle array device is arranged to have the same pattern as the microtiter plate so that commercial robotic liquid dispensing equipment can be used to fill the reservoirs of the microfluidic channels with samples, then tiling or combining a number of smaller microfluidic nozzle array devices (i.e., subunits) to form a larger structure can be used since the microtiter plates consist of regularly spaced sample input points in a grid pattern. For example, the microfluidic nozzle array devices can be formed and then combined with one another to produce a structure that has the desired number of sample reservoirs (also referred to as sample wells or sample inputs) to receive a desired number of samples. For example, some common microfluidic devices contain 96 sample reservoirs (8×12 grid); 384 sample reservoirs (16×24 grid); and 1536 sample reservoirs (32×48 grid). The tiling can be done by number of known conventional means, including by permanently bonding adjacent tiles together by melt bonding, welding, gluing, etc. In other words, any suitable method or technique for joining polymer structures together can be used. The subunit structures can be formed as individual subunit tiles (see FIGS. 17–18) or the subunit structure can be in the form of an elongated strip that includes a number of rows of nozzles. For example, the strip can be formed to include 2 rows of spaced apart nozzles.

Figure 17:
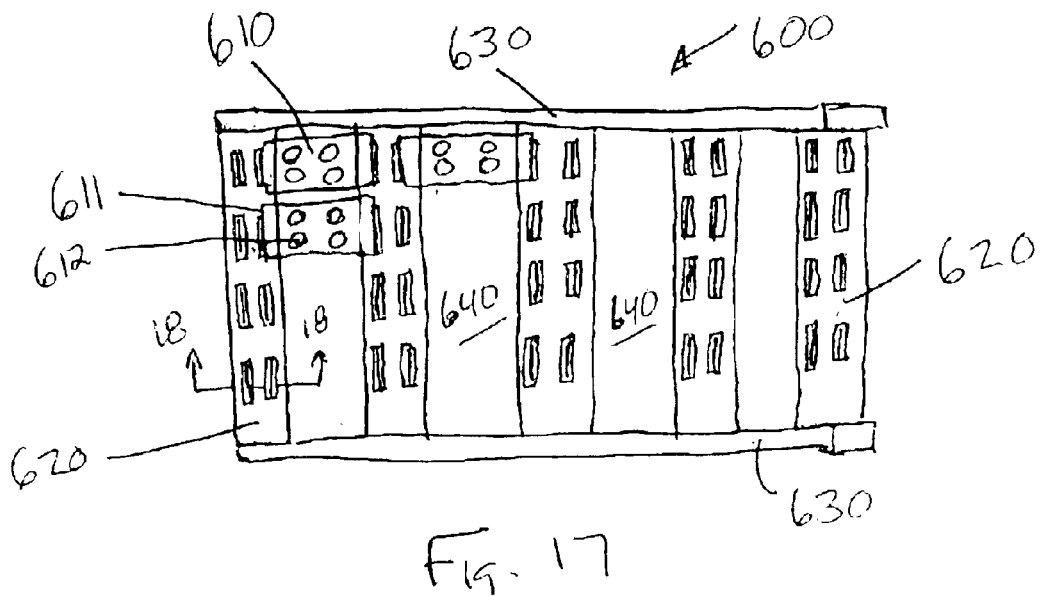
FIG. 17 is a top plan view of a retaining base for releasably holding a number of microfluidic nozzle subunit structures.

Alternatively, the user can be supplied with a base plate that has a number of features formed therein to permit nozzle subunit structures to be inserted into and retained by the base plate. For example, the base plate can contain pre-defined receptacles that receive the nozzle subunit structures in such a way that the nozzle subunit structures are securely held within the base plate and are arranged according to a desired pattern. One or both of the base plate and the nozzle subunit structures can contain interlocking features to provide an interlocking connection between the base plate and the nozzle subunit structures. In this embodiment, the base plate functions as a base on which the final microfluidic nozzle array device can be constructed by arranging a number of nozzle subunit structures together and then securely holding these subunit structures within the base plate. One exemplary structure for releasably holding the nozzle subunits in an interlocked manner is illustrated in FIG. 17 and is discussed in greater detail hereinafter in the discussion of Example 3.

There are a number of advantages that are obtained by tiling or otherwise combining a number of nozzle subunit structures into a microfluidic nozzle array device of greater dimension. First, the cost of manufacturing the mold for the smaller nozzle subunit structure is substantially less than the cost of manufacturing a mold for the entire grid of the microfluidic nozzle. Also, the cost of mold replacement is also substantially reduced in the case that only one pin in the mold is damaged. Second, the utility of the nozzle array is made more flexible. If an experiment does not require all of the reservoirs (e.g., 96) of the microfluidic device to be filled, only the needed number of nozzles or a number close thereto can be inserted into the base plate. At the same time, this construction still permits robotic dispensing of samples. For example and according to one exemplary embodiment, one nozzle subunit structure contains 4 reservoirs and therefore, if the experiment only requires 60 reservoirs, then only 15 nozzle subunit structures are inserted into the base plate. In this manner, the potential waste or inefficiency related to each microfluidic device is eliminated or greatly reduced because the number of unused reservoirs is greatly reduced or entirely eliminated.

Figure 10:
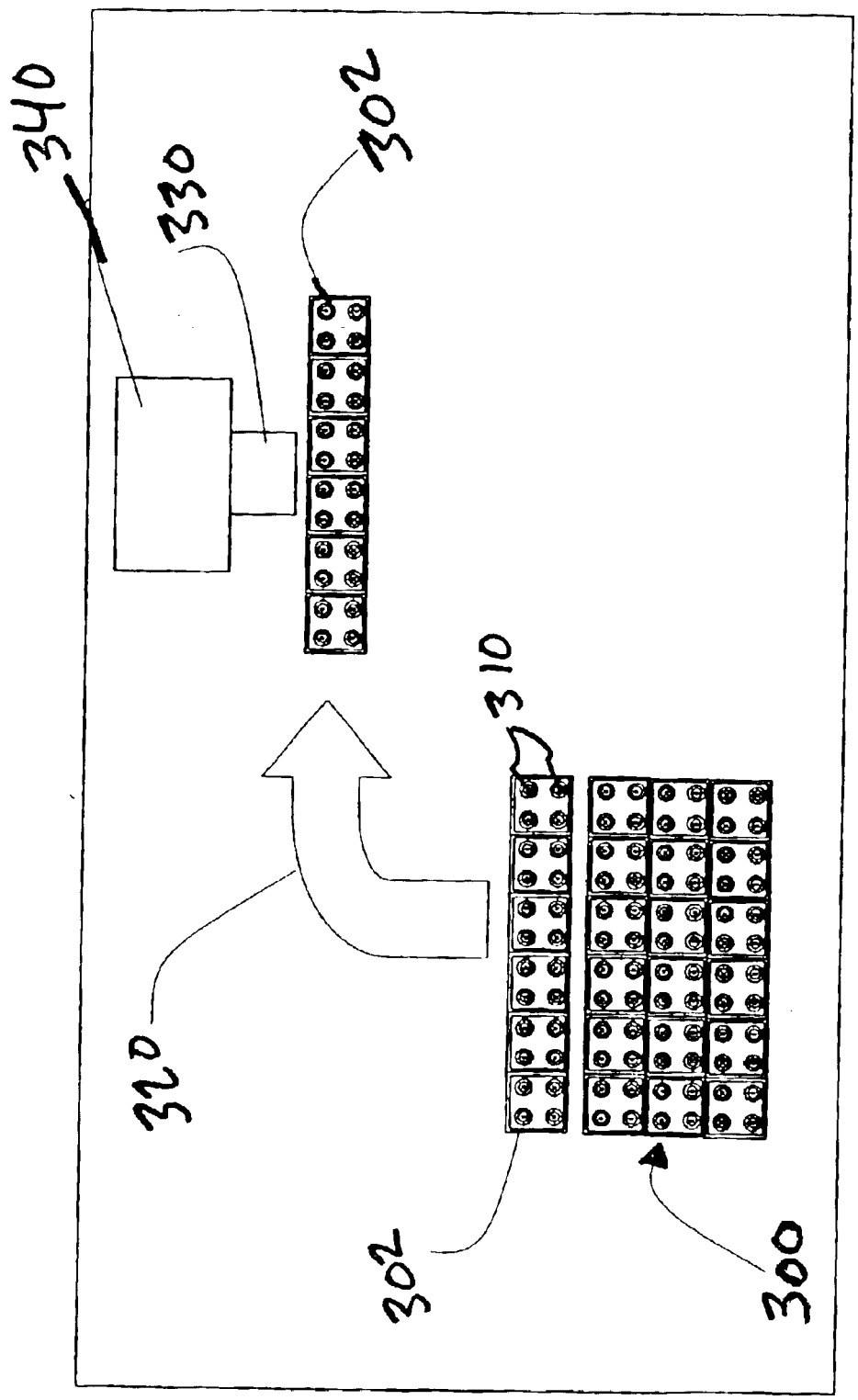
FIG. 10 is a top plan view of a tile arrangement formed of a number of strips connected to one another with each strip including a nozzle array, wherein one of the strips is removed and placed in close proximity to a mass spectrometer.

Third, when the microfluidic nozzle array device is used for electrospray or nanospray in front of a mass spectrometer inlet, a common configuration is to have the nozzle spray "off-axis", i.e., the nozzle sprays in a direction perpendicular to the inlet. Since the nozzle has to be placed in close proximity to the inlet (e.g., typically within an inch), there is often times not enough room in front of the inlet to accommodate the entire microtiter plate. FIG. 10 illustrates how a tiled microfluidic nozzle array microtiter plate can be used for electrospray in the off-axis configuration. A tiled microfluidic nozzle array 300 arranged in a 96 well microtiter plate format is broken up into strips 302 with two rows of 12 nozzles 310 each. One of the strips 302 is broken away or is otherwise removed from the others and is transferred (as indicated by arrow 320) to a nozzle mount (not shown) in front of a mass spectrometer inlet 330 of a mass spectrometer 340. The nozzle mount holds the strip 302 and has at least an x-y translation stage such that each of the nozzles can be placed in an optimal position with respect to the mass spectrometer inlet 330 for spraying of the sample material that is contained within the microfluidic channel associated with the selected nozzle. The direction of the spray is perpendicular to the mass spectrometer inlet 330. In schematic drawing of FIG. 10, the nozzles 310 are positioned below the centerline of the mass spectrometer inlet 330 and the spray is in the direction out of the surface of the drawing figure. It will be appreciated that the strips 302 that are still in tact can be used in future applications either by using the entire structure of joined strips 302 or by detaching one or more strips 302 for use in a given application depending upon the precise application and what the requirements for the application are in terms of the number of nozzles 310 that is needed.

The microfluidic nozzle array devices disclosed herein are suitable for use in a number of different types of applications.

For purposes of illustration only, some of the exemplary applications will be disclosed with reference to the microfluidic nozzle array device 100 illustrated in FIGS. 4–5; however, it will be understood that any of the devices disclosed herein can be used in place of device 100.

The microfluidic nozzle array device 100 is particularly suited for use in nanospray/electrospray applications. Electrospray is the technique that enables a liquid sample to be vaporized and ionized for mass spectrometry analysis. The electrospray process takes place in ambient pressure. Conventional electrospray utilizes a capillary with a relatively large inside diameter (i.e., about 50 μm) to deliver the liquid sample to the entrance of the mass spectrometer. The liquid that is flowing out of the capillary is vaporized under the influence of an electric field generated by placing a high voltage (e.g., 4–5 KV) on a metallic conductor close to the capillary opening and a ground plane opposite the capillary opening, or vice versa. Dry nitrogen flows through concentric tubing to the capillary to help nebulize the liquid flowing out of the capillary. The flow of the liquid inside the capillary is driven generally by a pump, such as a syringe pump.

For the nozzle array of the present microfluidic device 100 to be used as individual nanospray sources, the reservoir 160 on the opposite side of the nozzle opening is filled with a sample to be sprayed. Before the spray, the reservoir has to be sealed so that the reservoir is liquid tight. In other words, the open end of reservoir 160 (i.e., the open first end 142 of the microfluidic channel 140) must be sealed. The sealing of the open end of the reservoir 160 can be accomplished in a number of different ways that each provides a satisfactory liquid tight seal of the reservoir and permits the sample to be transported within the channel 140. FIGS. 11–13, illustrate a number of exemplary ways to provide the desired liquid tight seal of the reservoir.

For example, FIG. 11 illustrates a first sealing technique in which the opening of the reservoir 160 (i.e., the first end 142 of the microfluidic channel 140) is sealed with an elastic cover sheet 400. The elastic cover sheet 400 is preferably in the form of an elastic polymeric cover sheet. In the microfluidic nozzle array device 100, the polymeric cover sheet 400 is coupled to the reservoir wall 124 so that the polymeric cover sheet 400 extends completely across the open end of the reservoir 160. A mechanical plunger 410 or the like can be used to apply a force to the polymeric cover sheet 400 to force the sample along the length of the microfluidic channel 140 and ultimately out of the nozzle opening (second end 144 of thee microfluidic channel 140) in a continuous stream, generally indicated at 430. The discharged continuous liquid stream of the sample is then vaporized under the influence of an electric field. The general direction of movement of the polymeric cover sheet 400 and the plunger 410 is illustrate by arrow 420.

Another sealing technique is illustrated in FIG. 12. According to this technique, a movable sealing member 400 is provided and is formed of a sealing base 422 for sealing the opening of the reservoir and a rod or plunger 444 that is attached to the sealing base 442. The dimensions of the sealing base 442 are greater than the dimensions of the open end of the reservoir 160 and therefore, the sealing base 442 seats against the reservoir wall 124 and completely extends across the open end of the reservoir 160. The sealing base 442 is formed of a suitable elastic material to permit the sealing base to locally deform when a force is applied thereto. This elasticity permits the sealing base 442 to act as a temporary diaphragm that seals the reservoir as the sealing base 442 is directed into the reservoir 160 itself.

When the sealing base 442 is pushed downward in the direction toward the nozzle 170, the sealing base 442 deforms as it is forced into the first end of the microfluidic channel 140 (which is also the entrance to the reservoir 160). In the illustrated embodiment, the sealing base 442 includes a flange 446 that has a greater diameter than the diameter of the other portions of the sealing base and therefore, when the sealing base is inserted into the reservoir, the flange 446 intimately contacts the inner surface of the reservoir wall 124 and forms the liquid tight seal between the sealing base and the reservoir. As the sealing base 442 is inserted into the reservoir 160 and travels therein toward the nozzle, the sealing base 442 effectively forces the sample toward the second end 144 of the microfluidic channel 140, causing the sample to be discharged through the nozzle opening defined thereat. There may be an air gap between the sample (e.g., a liquid) in the reservoir 160 and the sealing base 442 or a vent (not shown) can be incorporated into the sealing base 442 for air to be pushed out of the reservoir 160 when the sample is forced through the microfluidic device by the sealing base 442. The vent can be fabricated using conventional vent technology in that the vent should permit air passage, while being impermeable to the flow of liquid so that the sample is prevented from flowing through the vent and out of the reservoir 160.

It will be appreciated that the plunger 444 can either be manually operated or it can be part of an automated system including an actuator or the like which controls the movement of the plunger 444. All of the plungers 444 can be linked to a common actuator or the link so that upon activation, the plungers 444 are all driven at the same time, resulting in the samples being concurrently transported through respective channels to respective nozzles.

Yet another sealing technique is illustrated with reference to FIG. 13 in which a fluid carrying member 450 is provided. The member 450 has a hollow portion and is generally shaped to be complementary to the shape of the reservoir 160 to permit the member 450 to seat against the upper edge of the reservoir wall 124. The member 450 includes a distal end 452 which initially is positioned proximate to the open end of the reservoir 160. At the distal end 452, a gasket 460 is provided and in the illustrated embodiment, the gasket 460 is in the form of a sealing O-ring or the like. The gasket 460 serves to provide a seal between the distal end 452 and the reservoir wall 124 to prevent from escaping between this interface when the sample is transported in the following manner. Because the member 450 is at least partially hollow, the gasket 460 is disposed around the bore that extends through the member 450.

In this embodiment, the sample is moved within the microfluidic channel 140 by conducting a fluid through the member 450 (more specifically, the bore thereof) to effectively force the sample through the microfluidic channel 140 to the nozzle 170 where the sample is discharged in continuous stream 430. The fluid is preferably a high-pressure gas, such as air or dry nitrogen gas that is delivered from a source that is in fluid communication with the piston bore. The flow direction of the fluid is generally indicated at 470. In another embodiment, the fluid can be the liquid sample fed into the microfluidic channel 140 to continuously push liquid out through the nozzle.

It will be appreciated that a protective cover (not shown) can be placed at the distal end 452 of the fluid carrying member 450 to prevent sample from contacting the inner surfaces of the piston bore. The protective cover must be permeable to the fluid that flows through the bore and into the reservoir 160 to transport the sample along the microfluidic channel 140. For example, the protective cover can be in the formed, of a thin polymeric film that is gas permeable, while at the same time being impermeable to liquid flow. In this manner, the sample can not contact the bore itself. The use of such a protective cover is not required since the injected fluid that flows through the member 450 can push the liquid sample out by applying a force to the air gap between the sample and the surrounding structure.

A more conventional fluid delivery mechanism can be used with the device 100. In this embodiment, a stopper is inserted into the reservoir 160, with the stopper having a bore formed therethrough which is in communication with the reservoir 160. A capillary is inserted through the bore and the liquid sample is injected into the reservoir through the capillary from a source external to the capillary. In this embodiment, the sample is not stored in the reservoir 160 but rather is delivered to the channel 140 by being injected into the reservoir 160 through the capillary.

As previously mentioned, the front face of the nozzle array is made electrically conducting by a thin film of metal or conducting polymer. When an electric field of appropriate strength is applied to the nozzle (e.g., as by the arrangement illustrated in FIG. 3), the liquid and the analytes it carries (i.e., the sample) are vaporized as they are discharged through the nozzle opening. Liquids that are suitable for use in electrospray mass spectrometry analysis include but are not limited to acetonitrile, methanol, ammonium acetate, and other volatile liquids. Since the inside diameter of the nozzle is less than about 20 $\mu$m, the amount of material flowing out of the nozzle to be vaporized is less than the amount that is typically used in a conventional electrospray operation. Also, the outside of 50 $\mu$m creates a strong enough electric field for vaporization with applied voltage below about 6 KV.

Figure 15:
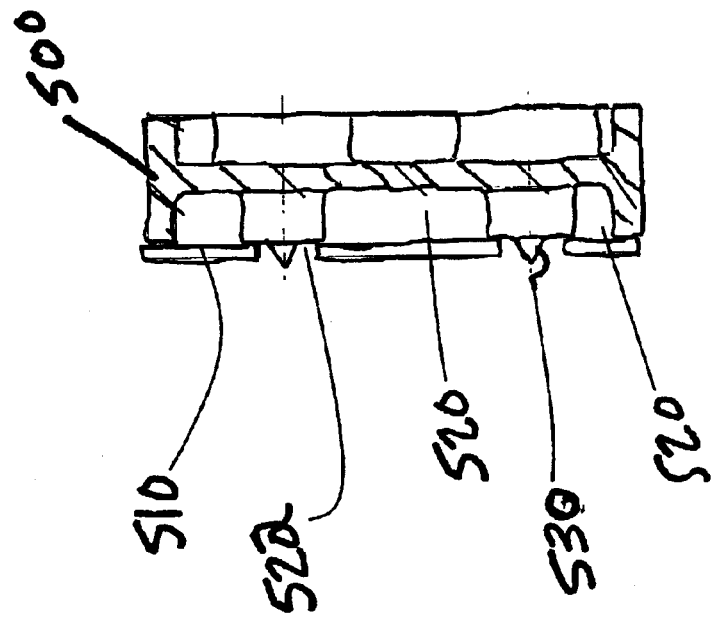
FIG. 15 is a cross-sectional view taken along the line 14—14.
Figure 14:
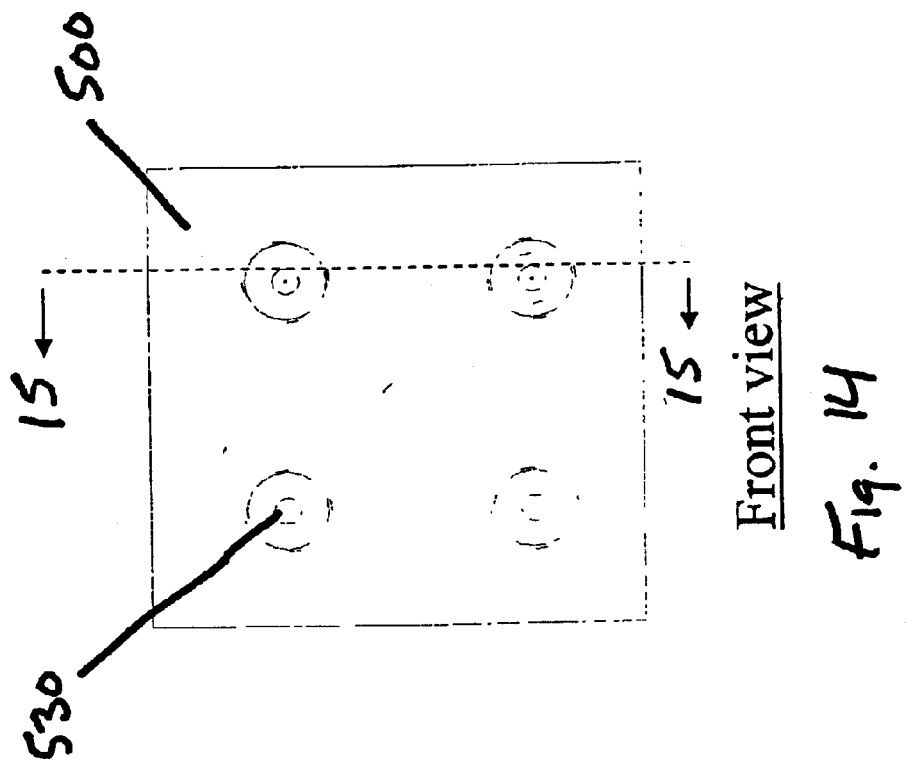
FIG. 14 is a top plan view of an exemplary microfluidic nozzle array device.

The use of a nebulizing gas to assist in the vaporization process is therefore not needed; however, if nebulizing gas is needed, channels conducting dry nitrogen gas to the nozzle opening may be easily added in a polymer substrate attached to the front of the nozzle array. FIGS. 14–15 are a top plan view and a cross-sectional view, respectively, of a microfluidic nozzle array device 500 in combination with a substrate 510 having gas conduits 520 formed therein for nebulization. The microfluidic nozzle array device 500 can be similar to or identical to any of the exemplary microfluidic array devices disclosed hereinbefore. A gas outlet 522 is formed such that it is concentric with one nozzle 530. The substrate 510 with the nebulizing gas channels can be fabricated by an injection molding process during the injection molding process that is used to the nozzle array device 500 itself or it can be fabricated first and then later attached to (e.g., bonded) the nozzle array device 500 as a separate component. The substrate 510 can be attached in any number of different ways including but not limited to using an adhesive or meltingly bonding the two members along a boundary zone.

In some instances, it may not be necessary to have the nozzle array conform to the microtiter plate sample well format. For example, the sample can be fed to the nozzle by the elutant of a high performance liquid phase gas chromatography (HPLC) column. Since the reservoir size in the nozzle array can be formed to arbitrary sizes, it can be formed so that the open end of the reservoir can receive one end of the HPLC column or any plumbing for splitting the HPLC elutant for mass spectrometry analysis. The reservoir side of the nozzle array can also consist of injection molded features for splitting elutant for mass spectrometry analysis. The driving force for the liquid sample analytes to flow through the nozzle opening in this case is the pressure-driven liquid flow of the HPLC. Neither a pressure diaphragm nor an external pressure-inducing mechanism is needed.

The microfluidic nozzle array devices disclosed herein are also particularly adapted to be used as a nozzle array for optical spectrometry. Since each microfluidic channel in the nozzle array device terminates with a nozzle opening having an inside diameter of 20 μm or less and the substrate of the nozzle array device is formed of a polymeric material which is generally hydrophobic, liquid inside the microfluidic channel does not drip or be discharged out of the nozzle without external force being applied thereto. When light, either ultraviolet or visible, is incident on the reservoir side of the array, the light will come out of the nozzle opening carrying the optical spectroscopic information of the analytes contained within the liquid in the microfluidic channel. The microfluidic channel and the nozzle opening thus provide an optical detection system without the use of optical windows. This is a significant advantage since the microfluidic nozzle array device does not have to be fabricated to incorporate optical windows made of an optical material in its design. This results in reduced structural complexity for the microfluidic nozzle array device and also a reduction in both cost and complexity relative to the fabrication of the microfluidic nozzle array device.

A 96 microtiter nozzle plate filled with samples can be placed in an ultraviolet reader for a 96 microtiter plate and spectrophotometric information for each sample can be obtained with the reader. A conventional microtiter plate used for UV spectrophotometry must have a sample well bottom made of a special UV transparent material in order to hold the sample inside the well and transmit UV light at the same time or a microtiter plate made of quartz must be used. The use of a microtiter nozzle plate array plate according to one exemplary embodiment thus allows two detection techniques for the samples in the plate without having to transfer the samples to other additional plates.

Figure 16:
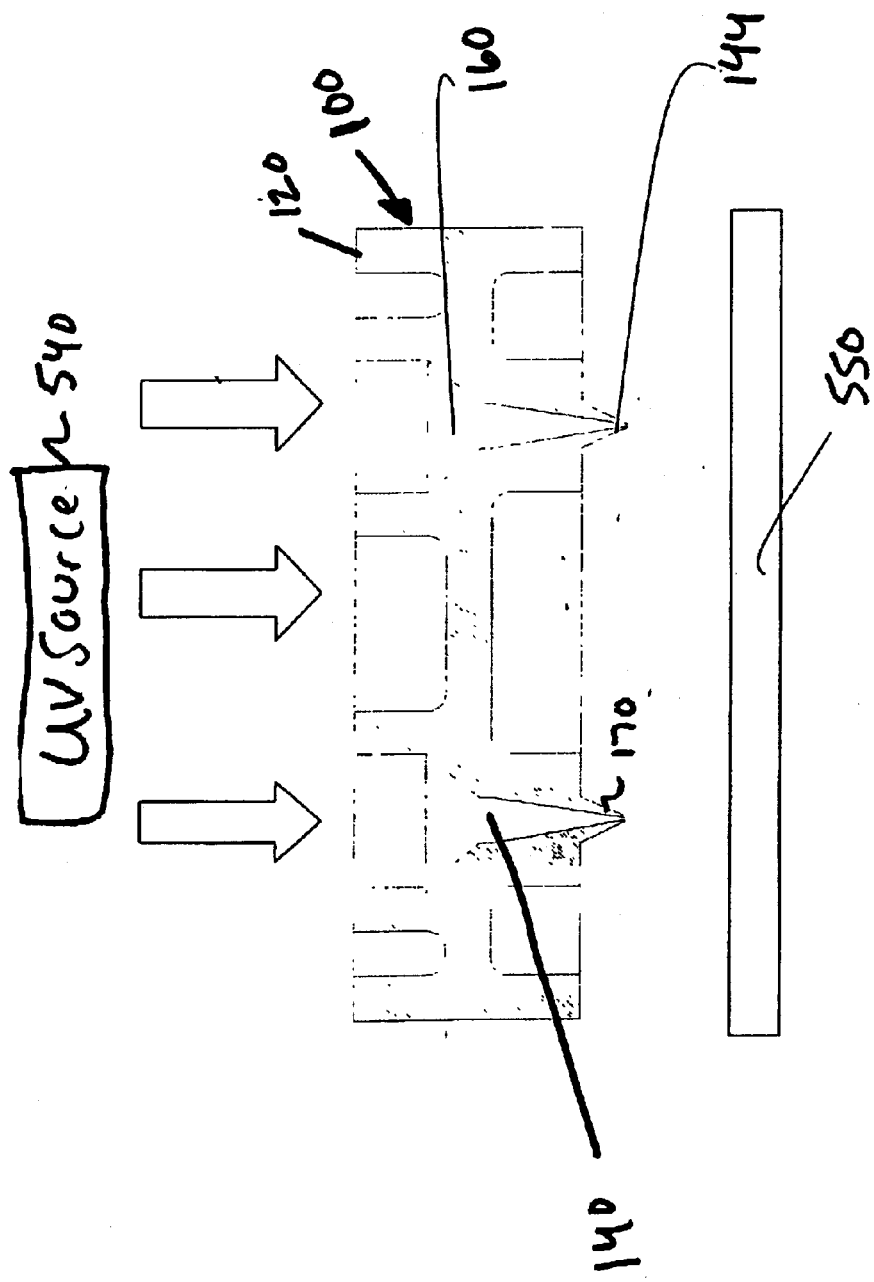
FIG. 16 is a cross-sectional side elevational view illustrating the microfluidic device of FIG. 5 being used in UV spectrophotometry.

FIG. 16 is a cross-sectional view illustrating how the microfluidic nozzle array device 100 can be used for UV spectrophotometry. FIG. 16 illustrates the microfluidic nozzle array device 100 in partial section showing two nozzle structures for purposes of illustrating the use of the microfluidic nozzle array device 100 in UV spectrophotometry. In this exemplary arrangement, UV light is emitted from a source 540 and travels toward the microfluidic nozzle array device 100 and is incident on the reservoir side 120. The UV light travels through the reservoir 160 and continues to travel along the length of the microfluidic channel 140, both of which hold the sample (e.g., liquid and analytes). The UV light travels through the nozzle opening 144 to a detector 550 that is disposed such that it faces the side of the microfluidic nozzle array device that contains the nozzles 170. The UV light carries the spectrophotometric information of the analyte is detected by the detector 550 of the UV reader. In this manner, the formation of perpendicular orientated microfluidic channels provides advantageously permits UV spectrophotometry to be carried out in an easy and convenient manner since the microfluidic nozzle array device 100 can easily be disposed between a UV light source and the detector 550 of the UV reader. Likewise, transmission fluorescence spectroscopy can be carried out using the microfluidic nozzle array device 100.

Unlike conventional microfluidic devices where optical windows formed of an optical material were fabricated in the devices, the substrate body of the present microfluidic nozzle array device does not have to be formed of an optically transparent material. This reduces the complexity of the fabrication process since this requirement is not present in the microfluidic nozzle array device.

The present microfluidic nozzle array devices disclosed herein also can be used in a wide range of other applications in which similar conventional devices have typically been used. For example, the microfluidic nozzle array device can be used for spotting DNA or protein array on a substrate instead of using the conventional capillary wicking methods that are now used with metallic capillaries. Presently, the DNA array spotting is primarily carried out by "wicking" DNA fragments into an open split end of a metallic capillary. To spot in an array format on a glass slide, the split end of the capillary is pressed slightly onto the glass slide by a robotic arm or the like to facilitate the deposition of the DNA fragments. On being lifted from the glass slide, the metallic capillary has a tendency to "spring" off the glass slide. As a result of this phenomena and other factors, it is common that about 20% of spots in the array are deficient in some way, e.g., either the spot is bare or an inadequate amount of material has been deposited. Spotting is typically carried out with a row of eight to twelve capillaries using an expensive machine and the capillaries are rinsed and reused for different DNA samples.

The present microfluidic nozzle array devices disclosed herein have smaller nozzles openings (e.g., 20 μm or less) than conventional nozzle constructions and a number of advantages can be realized using the present microfluidic nozzle array devices in comparison to the conventional metal capillaries. First, the injection-molded microfluidic nozzle array devices can be disposed of after each deposition. Thus, the time consuming rinsing process is eliminated and there is no risk of cross-contamination since the devices are not reused. Second, DNA or protein molecules are not adsorbed on the walls of the polymeric nozzle as they are adsorbed on metallic surfaces. The spotting is therefore more complete when the molecules leave the polymeric nozzle to be deposited on the glass slide. Third, a two dimensional nozzle spotter can be manufactured inexpensively thereby greatly increasing the speed of the spotting operation. Fourth, the deposition of the DNA or protein molecules from the polymeric nozzle can be assisted by pumping the molecules out of the nozzle with high pressure air using one of the aforementioned devices and/or with an electric field for electrospray.

The microfluidic nozzle array device can also be used for spotting the plate for matrix-assisted laser desorption ionization (MALDI), replacing the pipette and capillary spotting methods. For matrix-assisted laser desorption and ionization mass spectrometry, a dominant analytical technique for protein molecules and fragments of high molecular weight, the molecules to be analyzed are deposited on a layer of matrix material, usually UV-absorbant molecules that can be vaporized by a UV laser. The molecules of interest are thus carried into the gas phase and are ionized alongside the matrix molecules. Traditionally, the metallic (usually aluminum) MALDI plate is spotted manually with the use of micropipettes and more recently with capillaries. The efficiency of the ionization process will be enhanced if the metallized polymeric nozzles are used for spotting. The matrix material is first electrosprayed onto the aluminum MALDI plate which is held at ground potential, whereas the metal coated nozzle is held at high voltage or vice versa. The molecules of interest are then electrosprayed in a new nozzle onto the matrix material. The spraying allows the matrix molecules and the molecules of interest to be more evenly intermingled with one another, thus enhancing the efficiency of laser assisted desorption and ionization. The spotting of the MALDI plate may also be carried out with a two-dimensional array of nozzles for high throughput. Thus, the density of the nozzle array can be greatly increased and this permits the density of the spotting array to be increased. Accordingly, more testing or experimental sites are provided on the substrate as a result on the increased density in the spotting. It will also be appreciated that an electric field can also be used to assist in the spotting process. The electric field can be generated by using the arrangement illustrated in FIG. 3 or by some other type of suitable arrangement.

One will further appreciate that the manufacturing methods disclosed herein that are based on injection molding techniques can be used to make pipette tips for nano to picoliter dispensing. In other words, a mold can be fabricated and resin can be injected into the mold to form pipette tips that have an elongated body and terminate in a tip section that has a tip opening having an inside diameter of less than about 20 µm (with the tip section having an outside diameter of less than about 50 µm.

The following examples serve merely to illustrate several embodiments of the present microfluidic array devices and do not limit the scope of the present invention in any way.

EXAMPLE 1

A polymeric microfluidic nozzle array device is fabricated using the technology disclosed herein is by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tip (i.e., the diameter of the nozzle opening) being less than about 20 microns.

By polishing the conical surface of the mold that defines the nozzle, the outer surface of the nozzle is made much smoother and further the shape of the nozzles is more consistent from nozzle to nozzle and from mold run to mold run. By providing a smooth highly polished surface in the conical portion, the friction of the resin flow is reduced and this results in an increase in the accuracy and efficiency of the injection process. These techniques provide advantages when forming structures having very small dimensions, such as the nozzles of the present microfluidic device which have microscale features.

The microfluidic nozzle array device is then used as an electrospray device for spraying a liquid sample that is disposed within the microfluidic features formed in the microfluidic nozzle array device. As described in detail hereinbefore, the nozzle serves to spray the liquid sample into a fine mist through electric-field induced evaporation. In this example, a voltage of between 5–6 KV is applied to a conductive region formed around the nozzle tip in order to provide the necessary electric-field. The vaporized, ionized sample is then injected into an inlet of a mass spectrometer for analysis.

EXAMPLE 2

A polymeric microfluidic nozzle array device is fabricated using the technology disclosed herein by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tips (i.e., the diameter of the nozzle opening) being less than about 20 microns. The mold is constructed so that a microfluidic nozzle array strip is formed having two rows of twelve nozzles each.

Upon removing the molded microfluidic nozzle array strip, the above process is repeated to form one or more other microfluidic nozzle array strips. The microfluidic nozzle array strips are then placed side by side and adjacent strips are detachably secured to one another by applying an adhesive (e.g., glue) to an edge of the each of the strips. More specifically, the edges are heated so that the polymeric material softens and then the adjacent strips are joined together along these edges so that a fused bond results between the two edges that are brought into contact. Preferably, the fused bond between adjacent strips includes a weakened section (e.g., a score line or the like can be formed along the bond or the thickness of the bonded interface section between the two strips can be of reduced thickness) so that one strip can easily be detached from the other strip. Any remaining microfluidic strips are attached in the same manner to form a single, tiled microfluidic nozzle array device that contains a weakened section between the adjacent bonded microfluidic devices. The number of bonded microfluidic nozzle array strips will vary depending upon the desired overall size of the microfluidic nozzle array device and more particularly, the desired overall number of reservoirs and nozzles per each microfluidic device. In use, the single,

EXAMPLE 3

A polymeric microfluidic nozzle array device is fabricated using the technology disclosed herein by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tips (i.e., the diameter of the nozzle opening) being less than about 20 microns. The mold is constructed so that a microfluidic nozzle array strip is formed having two rows of twelve nozzles each.

Upon removing the molded microfluidic nozzle array strip, the above process is repeated to form one or more other microfluidic nozzle array strips. FIG. 17 generally illustrates the concept of tiling or otherwise combining a number of nozzle subunit structures into a microfluidic nozzle array device of greater dimension. A base plate 600 is provided and serves as the means for receiving a number of nozzle subunits structures, generally indicated at 610, in a manner in which the nozzle subunit structures 610 are releasably interlocked with the base plate 600. More specifically, the base plate 600 is a frame-like member having a predetermined number of retaining rails 620 that are affixed at their ends to a pair of end walls 630. The rails 620 are spaced apart from one another so that open slots 640 are formed between adjacent rails 620.

Figure 18:
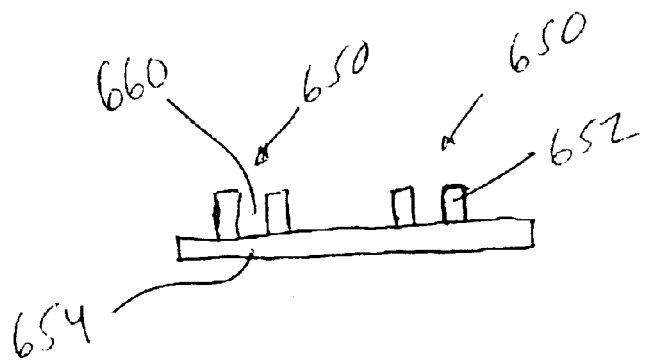
FIG. 18 is a cross-sectional view taken along the line 18—18 of FIG. 17.

As illustrated in FIGS. 17 and 18, each rail 620 has a number of clamping features 650 formed as a part thereof and spaced along the length of the rail 620. The clamping feature 650 includes side walls 652 that are spaced apart from one another to define a retaining slot 660 therebetween. The side walls 652 are disposed parallel to one another and extend upwardly from a floor 654 of the clamping feature 650. The distance between inner surfaces of the side walls 652 is selected so as to provide a frictional fit between a side wall of the nozzle subunit structure 610 so as to secure the structure 610 to the base 600 while at the same time permitting the structure 610 to be disengaged and easily removed from the base 600. Accordingly, the distance between the inner surfaces of the side walls 652 is equal to or slightly greater than a width of the side wall of the structure 610 that is received within the retaining slot 660 between the side walls 652.

Alternatively, the entire length of the rail 620 can have a "U-shaped" cross-section with a retaining slot 660 being formed between two side walls 652 that are spaced apart from one another. In this embodiment, the entire rail 620 serves as locking member instead of discrete clamping features 650 that are spaced along its length.

In the illustrated embodiment, each nozzle subunit structure 610 includes four nozzles 612 and four reservoirs (not shown) on the opposite side of the structure 610. For purpose of illustration only, the nozzles 612 are illustrated as facing away from the clamping features 650 (such that the nozzles 612 are in a plane above the clamping features 650); however, the structure 610 can be releasably interlocked with the base 600 such that the nozzles 612 face in the opposite direction. In other words, the reservoirs at the opposite end of the microfluidic channel face away from the clamping features 650 and are located in a plane above the clamping features 650.

The nozzle subunit structures 610 are releasably interlocked with the base 600 by inserting the two opposing side walls 611 of one nozzle subunit structure 610 into retaining slots 660 of two adjacent rails 620 that face another with an open slot 640 therebetween. One side wall 611 can be inserted first and then the other side wall 611 can be inserted into the other retaining slot 660 or both side walls 611 can be aligned with the slots 660 and then the nozzle subunit structure can be pressed downward to effectively dispose the side walls 611 within the retaining slots 660. Because both the nozzle subunit structure 610 and the base 600 are preferably formed of plastic materials and the dimensions of the structures are carefully selected, a frictional fit results when the side walls 611 are received within the retaining slots 660. When the side walls 611 are received within the retaining slots 660, the nozzles 612 and the reservoirs are received within the open slot 640 such that these elements are not obstructed by the base 600. In other words, the reservoir openings are clear so that samples can be injected or otherwise disposed within the reservoirs and also the nozzle openings are clear so that the sample can be discharged.

In one embodiment, the base 600 is formed of a polymeric material and is manufactured using an injection molding process such that the base 600 is formed as a unitary structure. While a frictional fit is one manner of releasably interlocking the nozzle subunit structures 610 to the base 600, a small amount of adhesive may be used at the interface between the side walls 611 and the clamping features 650 to ensure that the nozzle subunit structures 610 remain in place during various applications (when the base 600 may need to be turned upside down, etc.). Further, some applications require that a force be applied to the backside of the nozzle subunit structure 610 (e.g., due to actuation of a plunger in the reservoir, etc.) and therefore it is desirable for the nozzle subunit structures 610 to remain in place and not become dislodged from the base 600 when this force is applied. Any number of suitable adhesives can be used and it will be appreciated that one type of adhesive is a releasable adhesive that permits the nozzle subunit structure 610 to be removed from the base 600.

FIG. 19 illustrates another embodiment of base 600 that is very similar to the configuration illustrates in FIGS. 17–18. In this embodiment, the clamping features 650 are configured to receive two side walls 611 of adjacent nozzle subunit structures 610. Thus, the distance between the inner surfaces of the side walls 652 is selected so that the width of two side walls 611 placed in intimate adjacent contact with one another is about equal to or slightly less than the distance between the inner surfaces of the side walls 652. In other words, the slot 660 is configured to receive and retain two side walls 611 of adjacent nozzle subunit structures 610. To removeably couple the nozzle subunit structures 610 to the base 600 according to this embodiment, one side wall 611 is disposed within the slot 660 and then another side wall 611 of an adjacent nozzle subunit structure 610 is disposed in the slot 660 next to the other side wall 611, thereby providing a frictional fit that results in both adjacent nozzle subunit structures 610 being held securely in place. Unlike the embodiment of FIGS. 17–18, this embodiment requires that the two side walls 611 be disposed within one slot 660 to effectively couple each nozzle subunit structure to the base 600.

It will be appreciated that other clamping members can be used besides the above described ones. For example, each clamping member can consist of a spring biased clip that receives side wall 611 in a frictional manner so as to retain and hold the side wall 611 in a releasable manner. The clip can consist of two opposing plates that are hingedly connected at one end so as to bias the plates toward one another. The side wall 611 is received at the opposite ends of the plates inserting the side wall 611 between the plates and then directing the side wall 611 between the plates toward the hinged end. The biasing action between the plates ensures that the side wall 611 is securely gripped between the plates, while at the same time can be removed by simply overcoming the biasing force and lifting the side wall 611 upward until it is free of the plates.

While the invention has been particularly shown and described shown and described with reference to preferred embodiments thereof, it will be understood by those skilled in the art that various changes in form and details may be made therein without departing from the spirit and scope of the invention.

What is claimed is:

1. A microfluidic device comprising:
   an injection molded article including:
      a body having a first surface and an opposing second surface, the body having at least one channel formed therein and extending through the body from the first surface to the second surface, wherein the channel has a reservoir section that is open at the first surface; and at least one nozzle disposed along the second surface, the nozzle being in fluid communication with the channel such that one end of the channel terminates in a nozzle opening that is formed as part of the nozzle, wherein the device is formed of an injection moldable material.

2. The microfluidic device of claim 1, wherein the channel has a cylindrical shape along at least a substantial length thereof, the channel being defined by a seamless cylindrical surface.

3. The microfluidic device of claim 1, wherein the channel is inwardly tapered such that the dimensions of the channel are greatest in the reservoir section and are at a minimum at the nozzle opening.

4. The microfluidic device of claim 1, wherein the channel is formed in the reservoir section so that it is substantially perpendicular to both the first and second surfaces.

5. The microfluidic device of claim 1, wherein the at least one nozzle extends beyond the second surface and is substantially conically shaped.

6. The microfluidic device of claim 5, wherein the nozzle has an outside diameter equal to or less than about 50 $\mu$m.

7. The microfluidic device of claim 1, wherein the nozzle has an outside diameter equal to or less than about 100 $\mu$m.

8. The microfluidic device of claim 1, wherein the nozzle opening has a diameter equal to or less than about 20 $\mu$m.

9. The microfluidic device of claim 1, wherein the nozzle opening has a diameter equal to or less than about 50 $\mu$m.

10. The microfluidic device of claim 1, wherein a portion of the channel that is formed in the nozzle and that terminates in the nozzle opening is inwardly tapered toward the nozzle opening.

11. The microfluidic device of claim 1, wherein the at least one channel and the at least one nozzle are arranged in a geometrical array.

12. A The microfluidic device of claim 1, further including:
a conductive region formed on the second surface around a periphery of the at least one nozzle.

13. The microfluidic device of claim 12, wherein the conductive region is formed of metal and is electrically connected to an electric contact.

14. The microfluidic device of claim 13, wherein the electrical contact is formed on the second surface along a single edge of the body.

15. The microfluidic device of claim 1, wherein the channel has a first section in which inner channel surfaces are parallel, the first section at least partially defining the reservoir section and extending to the first surface, the channel further including a second section in which the inner channel surfaces are in a non-parallel relationship, the second section extending from the first section to the nozzle opening.

16. A microfluidic device comprising: an injection molded microfluidic device formed of an injection moldable material comprising:
a body having a first surface and an opposing second surface, the body having at least one channel formed therein, the channel extending through the body from the first surface to the second surface, wherein the channel has a reservoir section that is open at the first surface for receiving a sample; and
at least one nozzle integrally formed with the body and disposed along and extending beyond the second surface, the nozzle being defined by outer surfaces that are non-parallel in nature and the number of nozzles being equal to the number of channels with each nozzle having a section of the channel formed therethrough such that each channel terminates in a nozzle opening of the nozzle, wherein a diameter of the nozzle opening is equal to or less than about 100 $\mu$m and an outside diameter of the nozzle is equal to or less than about 150 $\mu$m and wherein the channel section formed in the nozzle is defined by non-parallel surfaces that terminate at one end with the formation of the nozzle opening.

17. The microfluidic device of claim 16, wherein a diameter of the nozzle opening is equal to or less than about 150 $\mu$m and an outside diameter of the nozzle is equal to or less than about 100 $\mu$m.

18. The microfluidic device of claim 16, wherein a diameter of the nozzle opening is equal to or less than about 20 $\mu$m and an outside diameter of the nozzle is equal to or less than about 50 $\mu$m.

19. The microfluidic device of claim 16, further including:
a device for sealing the reservoir section and for transporting the sample from the reservoir section through the channel to the nozzle opening where the sample is discharged.

20. The microfluidic device of claim 16, further including:
a seal in the form of a deformable, elastic polymeric cover sheet that is initially disposed across an open end of the reservoir section such that it is attached to and across the first surface and a shaft for engaging the polymeric cover sheet, wherein when the shaft is driven to an extended position, the polymeric cover sheet is deformed and forms a seal with an inner surface of the reservoir section and forces the sample to flow toward the nozzle opening where it is discharged.

21. The microfluidic device of claim 19, wherein the transport device comprises a displaceable member including a base with a deformable seal extending therearound, the base being initially disposed across an open end of the reservoir section with a shaft being connected to the base, wherein when the shaft is driven to an extended position, the base is received within the reservoir section and the flange forms a seal with an inner surface of the reservoir section and forces the sample to flow toward the nozzle opening where it is discharged.

22. The microfluidic device of claim 19, wherein the transport device comprises a member having a bore formed therethrough with a gasket being disposed at a distal end of the member, the gasket forming a seal between the member and the reservoir section, wherein the member is in communication with a source of fluid that is introduced into the reservoir section to force the sample to flow toward the nozzle opening where it is discharged.

23. The microfluidic device of claim 22, wherein the fluid comprises a gas.

24. The microfluidic device of claim 22, wherein the fluid comprises the sample.

25. The microfluidic device of claim 22, wherein the gasket comprises an O-ring that is disposed between the distal end and the first surface of the body, the O-ring being free of interference with the fluid flowing through the bore into the reservoir section.

26. The microfluidic device of claim 16, wherein the body and the at least one nozzle comprise a single injection-molded structure that is formed of a polymeric material.

27. The microfluidic device of claim 16, wherein the at least one nozzle comprises an array of nozzles arranged according to a predetermined pattern along the second surface of the body.

28. The microfluidic device of claim 27, wherein the nozzle array includes a predetermined number of nozzles arranged in axial rows across the second surface.

29. A detection system for detecting one or more properties of a sample, the detection system including:
- an injection molded microfluidic device formed of an injection moldable material comprising:
  - a body having a first surface and an opposing second surface, the body having at least one channel formed therein, the channel extending through the body from the first surface to the second surface, wherein the channel has a reservoir section that is open at the first surface; and
  - at least one nozzle integrally formed with the body and disposed along and extending beyond the second surface, the nozzle defined by outer surfaces that are non-parallel in nature and the number of nozzles equal to the number of channels with each nozzle having a section of the channel formed therethrough such that each channel terminates in a nozzle opening that is formed as part of the nozzle, wherein a diameter of the nozzle opening is equal to or less than about 100 µm and an outside diameter of the nozzle is equal to or less than about 150 µm and wherein the channel section formed in the nozzle is defined by tapered inner surfaces that terminate at one end with the formation of the nozzle opening; and
- a detector for receiving the sample discharged from the microfluidic device through the nozzle opening thereof, wherein the detector analyzes the discharged sample and provides information regarding one or more properties of the sample.

30. The detection system of claim 29, wherein the detector is a mass spectrometer.

31. The detection system of claim 29, wherein the diameter of the nozzle opening is equal to or less than 20 µm and the outside diameter of the nozzle is equal to or less than 50 µm.

32. The detection system of claim 29, wherein the body includes a thin conductive film disposed on the second surface around each nozzle, the conductive film being connected to a source of electricity so that when an electric field is applied to the conductive film, the sample is vaporized and ionized as it is discharged through the nozzle opening.

33. A The detection system of claim 29, wherein the sample is formed of a liquid and analytes.

34. The detection system of claim 33, wherein the detector is a mass spectrometer and the liquid comprises a water and at least one component selected from the group consisting of acetonitrile, methanol, and ammonium acetate.

35. The detection system of claim 29, further including:
- a device for sealing the reservoir section and for transporting the sample from the reservoir section through the channel to the nozzle opening where the sample is discharged.

36. The detection system of claim 35, wherein the transport device comprises a displaceable member including a deformable, elastic polymeric cover sheet that is initially disposed across an open end of the reservoir section and a shaft that is connected to the polymeric cover sheet, wherein when the shaft is driven to an extended position, the polymeric cover sheet forms a seal with an inner surface of the reservoir section and forces the sample to flow toward the nozzle opening where it is discharged.

37. The detection system of claim 35, wherein the transport device comprises a displaceable member including a base with a deformable seal extending therearound, the base being initially disposed across an open end of the reservoir section with a shaft being connected to the base, wherein when the shaft is driven to an extended position, the base is received within the reservoir section and the flange forms a seal with an inner surface of the reservoir section and forces the sample to flow toward the nozzle opening where it is discharged.

38. The detection system of claim 35, wherein the transport device comprises a member having a bore formed therethrough with a gasket being disposed at a distal end of the member, the gasket forming a seal between the member and the reservoir section, wherein the member is in communication with a source of fluid that is introduced into the reservoir section under predetermined conditions to force the sample to flow toward the nozzle opening where it is discharged.

39. The detection system of claim 38, wherein the fluid comprises a gas.

40. A process for creating a vaporized and ionized fluid stream from a liquid sample for injection into a diagnostic device, the process comprising the steps of:
- providing an injection molded microfluidic device formed of an injection moldable material comprising:
  - a body having a first surface and an opposing second surface, the body having at least one channel formed therein, the channel extending through the body from the first surface to the second surface, wherein the channel has a reservoir section that is open at the first surface; and
  - at least one nozzle integrally formed with the body and disposed along and extending beyond the second surface, the number of nozzles equal to the number of channels with each nozzle being in fluid communication with one channel such that each channel terminates in a nozzle opening that is formed as part of the nozzle, wherein a diameter of the nozzle opening is equal to or less than about 50 µm and an outside diameter of the nozzle is equal to or less than about 100 µm;
- disposing a sample in the channel at least within the reservoir section;
- transporting the sample from the reservoir to the nozzle tip where the sample is discharged; and
- applying an electric field to the second surface of the body around each nozzle, the electric field being of sufficient strength so as to cause the discharged sample to be vaporized and ionized.

41. The process of claim 40, wherein the diameter of the nozzle opening is equal to or less than 50 µm and the outside diameter of the nozzle is equal to or less than about 100 µm.

42. The process of claim 40, wherein the step of transporting the sample comprises:
- providing a transportation mechanism at the first surface adjacent the open reservoir section; and
- manipulating the transportation mechanism to cause a force to be applied to the sample in the direction toward the nozzle opening such that the sample flows to and is discharged through the nozzle opening.

43. The process of claim 42, wherein the transportation mechanism includes a displaceable member having a deformable, elastic polymeric cover sheet and a shaft coupled to the polymeric cover sheet and wherein the step of manipulating the mechanism includes the step of driving the shaft from a retracted position to an extended position, the polymeric cover sheet forming a seal with an inner surface of the reservoir section and wherein the polymeric cover sheet forces the sample to flow to and be discharged through the nozzle opening as the shaft is driven to the extended position.

44. The process of claim 42, wherein the transportation mechanism includes a displaceable member having a base with a sealing flange extending therearound and a shaft coupled to the base and wherein the step of manipulating the mechanism includes the step of driving the shaft from a retracted position to an extended position, the flange forming a seal with an inner surface of the reservoir section and wherein the base forces the sample to flow to and be discharged through the nozzle opening as the shaft is driven to the extended position.

45. The process of claim 42, wherein the transportation mechanism includes a member having a bore formed therethrough with a gasket providing a seal between the member and the first surface of the body, the bore being in communication with a fluid source at one end and with the reservoir section at the other end and wherein the step of manipulating the mechanism includes causing the fluid to flow through the bore and into reservoir section where it applies a force to the sample, resulting in the sample being discharged from the nozzle opening.

46. A process for array spotting on a substrate, the process comprising the steps of:

providing a microfluidic device comprising: an injection molded microfluidic device formed of an injection moldable material comprising:

a body having a first surface and an opposing second surface, the body having at least one channel formed therein, the channel extending through the body from the first surface to the second surface, wherein the channel has a reservoir section that is open at the first surface for receiving a sample; and a plurality of nozzles integrally formed with the body and disposed along and extending beyond the second surface, each nozzle defined by outer surfaces that are non-parallel in nature and the number of nozzles equal to the number of channels with each nozzle having a section of the channel formed therethrough such that each channel terminates in a nozzle opening that is formed as part of the nozzle, wherein a diameter of the nozzle opening is equal to or less than about 100 $\mu$m and an outside diameter of the nozzle is equal to or less than about 150 $\mu$m and wherein the channel section formed in the nozzle is defined by tapered inner surfaces that terminate at one end with the formation of the nozzle opening;

disposing one or more samples within the plurality of reservoir sections, with only one sample being disposed in one reservoir section;

positioning the microfluidic device proximate to the substrate with the plurality of nozzles facing the substrate; and transporting each sample from one reservoir to a respective nozzle tip where the sample is discharged through the nozzle opening onto the substrate to form a sample spot on the substrate.

47. The process of claim 46, wherein the diameter of the nozzle opening is equal to or less than about 20 $\mu$m and the outside diameter of the nozzle is equal to or less than about 50 $\mu$m.

48. The process of claim 46, wherein the samples contain DNA segments so that the resulting array of spots is a DNA array spotting.

49. The process of claim 46, wherein the samples contain protein molecules so that the resulting array of spots is a protein array spotting.

50. The process of claim 46, further including the step of:

pumping the sample through channel to the nozzle opening with high pressure air that is directed into the reservoir section.

51. The process of claim 46, further including the step of:

applying an electric field to the second surface of the body around each nozzle, the electric field being of sufficient strength so as to cause the discharged sample to be vaporized and ionized.

52. A microfluidic device comprising:

an injection molded article including:

a body having a first surface and an opposing second surface, the body having at least one channel formed therein and extending through the body from the first surface to the second surface, wherein the channel has a reservoir section that is open at the first surface; and at least one nozzle disposed along the second surface and having a length of the channel formed therethrough such that one end of the channel terminates in a nozzle opening that is formed as a distal end of the nozzle, wherein the device is formed of an injection moldable material and the length of channel formed in the nozzle has a varying diameter.

53. The microfluidic device of claim 52, wherein the nozzle is defined by tapered outer surfaces that terminate at one end with the nozzle opening.

54. The microfluidic device of claim 52, wherein the diameter of the channel formed in the nozzle is at a minimum at the nozzle opening.

55. The microfluidic device of claim 52, wherein the nozzle has a continuously varying diameter.

56. The microfluidic device of claim 52, wherein wall that defines the length of channel formed in the nozzle extends linearly along its length.

* * * * *